(12) United States Patent
Endo

(10) Patent No.: US 9,513,263 B2
(45) Date of Patent: *Dec. 6, 2016

(54) ULTRASONIC MEASUREMENT APPARATUS, ULTRASONIC HEAD UNIT, ULTRASONIC PROBE, AND ULTRASONIC IMAGING APPARATUS

(71) Applicant: SEIKO EPSON CORPORATION, Tokyo (JP)

(72) Inventor: Kogo Endo, Nagano (JP)

(73) Assignee: Seiko Epson Corporation, Tokyo (JP)

( * ) Notice: Subject to any disclaimer, the term of this patent is extended or adjusted under 35 U.S.C. 154(b) by 257 days.

This patent is subject to a terminal disclaimer.

(21) Appl. No.: 14/333,894

(22) Filed: Jul. 17, 2014

(65) Prior Publication Data

US 2015/0027228 A1    Jan. 29, 2015

(30) Foreign Application Priority Data

Jul. 26, 2013  (JP) ................................. 2013-155347

(51) Int. Cl.
*G01N 29/26*    (2006.01)
*G01N 29/24*    (2006.01)
(Continued)

(52) U.S. Cl.
CPC ........... *G01N 29/262* (2013.01); *A61B 8/4494* (2013.01); *G01N 29/0654* (2013.01);
(Continued)

(58) Field of Classification Search
CPC .............. G01N 29/262; G01N 29/2437; G01N 29/0654; G01N 2291/106
(Continued)

(56) References Cited

U.S. PATENT DOCUMENTS 7,115,980 B2 * 10/2006 Miyagawa .......... G02F 1/13452
257/668
7,226,417 B1 *  6/2007 Eberle ................... B06B 1/0633
29/25.35

(Continued)

FOREIGN PATENT DOCUMENTS

JP            2005-341085 A     12/2005

*Primary Examiner* — J M Saint Surin
(74) *Attorney, Agent, or Firm* — Global IP Counselors, LLP

(57) ABSTRACT

An ultrasonic measuring apparatus includes an ultrasonic transducer device having a substrate and an ultrasonic transducer element array that is arranged on the substrate, a first channel terminal group arranged at one edge portion of the ultrasonic transducer element array in a first direction, a second channel terminal group arranged at the other edge portion of the ultrasonic transducer element array in the first direction, a first flexible substrate provided on the one edge portion side and having arranged thereon a first wiring group that is connected to the first channel terminal group, a first integrated circuit apparatus that is mounted on the first flexible substrate and performs at least one of signal transmission to the first channel terminal group and signal reception from the first channel terminal group, a second flexible substrate provided on the other edge portion side and having arranged thereon a second wiring group that is connected to the second channel terminal group, and a second integrated circuit apparatus that is mounted on the first flexible substrate and performs at least one of signal transmission to the second channel terminal group and signal reception from the second channel terminal group. In the ultrasonic transducer element array, channels that are connected to the first channel terminal group and channels that are connected to the second channel terminal group are arranged alternately every channel in a second direction that intersects the first direction.

14 Claims, 20 Drawing Sheets

(51) Int. Cl.
*G01N 29/06* (2006.01)
*G01N 29/34* (2006.01)
*A61B 8/00* (2006.01)

(52) U.S. Cl.
CPC ....... *G01N 29/2437* (2013.01); *G01N 29/343* (2013.01); *G01N 2291/106* (2013.01)

(58) Field of Classification Search
USPC .......................................................... 73/641
See application file for complete search history.

(56) References Cited

U.S. PATENT DOCUMENTS

2014/0116148 A1* 5/2014 Endo ...................... G01H 11/08
 73/661
2015/0029818 A1* 1/2015 Endo ........................ A61B 8/13
 367/7

* cited by examiner

FIG. 2A

| MAIN APPLICATION | LYMPHEDEMA<br>EDEMA PROGNOSIS, etc. | DECUBITUS<br>CONTROL | SKIN<br>COLLAGEN FIBERS | MUSCLE / TENDON<br>TREATMENT EVALUATION |
|---|---|---|---|---|
| DEPTH | ~80mm | ~50mm | ~30mm | ~80mm |
| HEAD LENGTH | 40mm | 40mm | 40mm | 40mm |
| FREQUENCY | 5MHz | 7MHz | 20MHz | 5MHz~ |

FIG. 2B

| FREQUENCY | 3.5MHz | 7.5MHz | 7.5MHz | 7.5MHz |
|---|---|---|---|---|
| HEAD LENGTH | 38~40mm | 25~26mm | 38~40mm | 38~40mm |
| NO. OF CHANNELS | 64 | 64 | 128 | 128 |
| NO. OF TRANSMISSION / RECEPTION CHs | 8 | 8 | 8 | 16 |
| HORIZONTAL RESOLUTION | 3mm | 2mm | 0.5mm | 0.5mm |

| CHANNEL | 1 | IC2 (120) 2 | 3 | IC2 4 | 5 | IC2 6 | 7 | IC2 8 | 9 | IC2 10 | 11 | IC2 12 | ... |
|---|---|---|---|---|---|---|---|---|---|---|---|---|---|
| T1 | P1 | P2 | P3 | P4 | P5 | P6 | P7 | P8 | | | | | |
| T2 | | P1 | P2 | P3 | P4 | P5 | P6 | P7 | P8 | | | | |
| T3 | | | P1 | P2 | P3 | P4 | P5 | P6 | P7 | P8 | | | |
| T4 | | | | P1 | P2 | P3 | P4 | P5 | P6 | P7 | P8 | | |
| T5 | | | | | P1 | ... | P3 | P4 | P5 | P6 | P7 | P8 | |
| ... | IC1 (110) | | IC1 | | IC1 | | IC1 | | IC1 | | IC1 | | |

(SCANNING PERIOD)

FIG.10

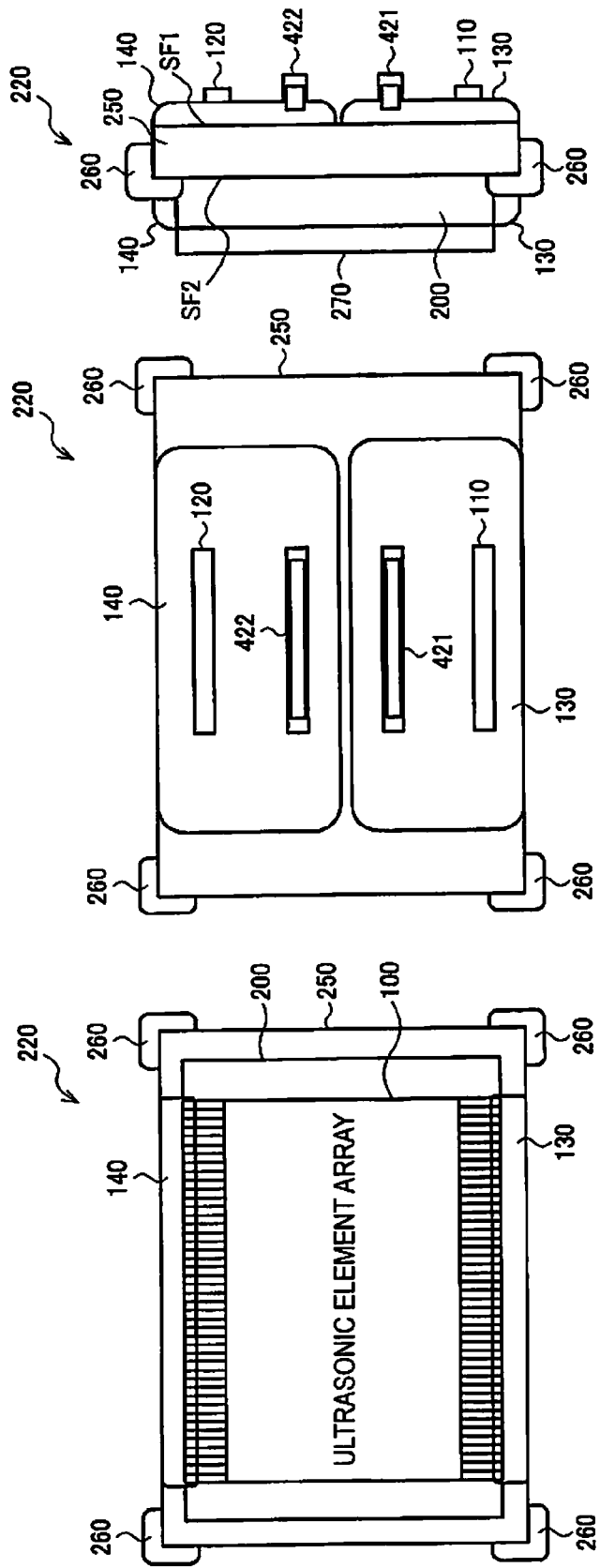

ULTRASONIC MEASUREMENT APPARATUS, ULTRASONIC HEAD UNIT, ULTRASONIC PROBE, AND ULTRASONIC IMAGING APPARATUS

BACKGROUND

1. Technical Field

The present invention relates to an ultrasonic measurement apparatus, an ultrasonic head unit, an ultrasonic probe, an ultrasonic imaging apparatus, and the like.

2. Related Art

Heretofore, bulk piezoelectric members have been used as ultrasonic transducer elements that transmit and receive ultrasonic waves. For example, JP-A-2005-341085 discloses an ultrasonic probe in which an insulator layer is provided from a portion of a back surface electrode of a bulk piezoelectric member to a lateral surface of the piezoelectric member, a conductor layer is provided continuously with a front surface electrode of the piezoelectric member so as to wrap around to the back surface electrode side, and wiring formed in a flexible substrate is connected to the conductor layer and the back surface electrode on the back surface side of the piezoelectric member.

A high voltage of around 100 V, for example, is needed in order to drive a bulk piezoelectric member, thus requiring the use of ICs having a high breakdown voltage. There is a problem in that ICs having a high breakdown voltage typically take up a large mounting area and the number of ICs increases, thus making it difficult to miniaturize an apparatus equipped with such ICs.

SUMMARY

An advantage of some aspects of the invention is to provide an ultrasonic measurement apparatus, an ultrasonic head unit, an ultrasonic probe, ultrasonic imaging apparatus and the like that enable device miniaturization to be realized.

An aspect of the invention relates to an ultrasonic measuring apparatus that includes an ultrasonic transducer device having a substrate and an ultrasonic transducer element array that is arranged on the substrate, a first channel terminal group arranged at one edge portion of the ultrasonic transducer element array in a first direction, a second channel terminal group arranged at the other edge portion of the ultrasonic transducer element array in the first direction, a first flexible substrate provided on the one edge portion side and having arranged thereon a first wiring group that is connected to the first channel terminal group, a first integrated circuit apparatus that is mounted on the first flexible substrate and performs at least one of signal transmission to the first channel terminal group and signal reception from the first channel terminal group, a second flexible substrate provided on the other edge portion side and having arranged thereon a second wiring group that is connected to the second channel terminal group, and a second integrated circuit apparatus that is mounted on the first flexible substrate and performs at least one of signal transmission to the second channel terminal group and signal reception from the second channel terminal group. In the ultrasonic transducer element array, channels that are connected to the first channel terminal group and channels that are connected to the second channel terminal group are arranged alternately every channel in a second direction that intersects the first direction.

According to an aspect of the invention, a first channel terminal group and a first flexible substrate are arranged at one edge portion of an ultrasonic transducer element array, a second channel terminal group and a second flexible substrate are arranged at the other edge portion, and channels that are connected to the first channel terminal group and channels that are connected to the second channel terminal group are arranged alternately in the second direction. It thereby becomes possible to miniaturize the apparatus.

Also, in an aspect of the invention, in a first scanning period, the first integrated circuit apparatus may transmit odd-numbered pulse signals, among 1st to kth pulse signals (where k is a natural number of 2 or more) to channel terminals belonging to the first channel terminal group, among 1st to kth channel terminals, and the second integrated circuit apparatus may transmit even-numbered pulse signals, among the 1st to kth pulse signals, to channel terminals belonging to the second channel terminal group, among the 1st to kth channel terminals, and in a second scanning period subsequent to the first scanning period, the second integrated circuit apparatus may transmit the odd-numbered pulse signals to channel terminals belonging to the second channel terminal group, among 2nd to k+1th channels, and the first integrated circuit apparatus may transmit the even-numbered pulse signals to channels belonging to the first channel terminal group, among the 2nd to k+1th channels.

According to this configuration, a scanning operation can be performed in an aspect of the invention in which channels that are connected to the first channel terminal group and channels that are connected to the second channel terminal group are arranged alternately.

Also, in an aspect of the invention, the ultrasonic measurement apparatus may include a processing part that outputs a control command for controlling transmission in the first scanning period and the second scanning period to the first integrated circuit apparatus and the second integrated circuit apparatus, and the first integrated circuit apparatus and the second integrated circuit apparatus may each include a plurality of transmission circuits that transmit pulse signals, and a control part that controls the plurality of transmission circuits based on the control command.

According to this configuration, a plurality of transmission circuits are able to transmit pulse signals in the first scanning period and the second scanning period, as a result of the processing part outputting a control command, and each integrated circuit apparatus controlling the plurality of transmission circuits based on the control command.

Also, in an aspect of the invention, the ultrasonic measurement apparatus may include a processing part that performs reception processing of reception signals, and the processing part may perform the reception processing, based on the reception signals from the first channel terminal group and the reception signals from the second channel terminal group obtained by the first integrated circuit apparatus and the second integrated circuit apparatus transmitting signals.

According to this configuration, reception processing of reception signals from the first channel terminal group and reception signals from the second channel terminal group is performed by the processing part, thus enabling the reception signals of a plurality of channels to be combined in the reception processing which includes reception focusing and the like, for example.

Also, in an aspect of the invention, in the ultrasonic transducer element array, 1st to Nth channels (where N is a natural number of 2 or more) may be arranged in the second direction, the first channel terminal group may be connected to odd-numbered channels, among the 1st to Nth channels, and the second channel terminal group may be connected to even-numbered channels, among the 1st to Nth channels.

According to this configuration, channels that are connected to the first channel terminal group and channels that are connected to the second channel terminal group can be arranged alternately every channel.

Also, in an aspect of the invention, the first integrated circuit apparatus may be mounted such that a long-side direction of the first integrated circuit apparatus coincides with a third direction that is a direction coinciding with the edge connecting the first flexible substrate to the first channel terminal group, and the second integrated circuit apparatus may be mounted such that a long-side direction of the second integrated circuit apparatus coincides with a fourth direction that is a direction coinciding with the edge connecting the second flexible substrate to the second channel terminal group.

Also, in an aspect of the invention, the first integrated circuit apparatus may have a plurality of transmission circuits that are arranged in the third direction and transmit a signal to the first channel terminal group, and the second integrated circuit apparatus may have a plurality of transmission circuits that are arranged in the fourth direction and transmit a signal to the second channel terminal group.

According to this configuration, the first integrated circuit apparatus is able to output a transmission signal to channels that are connected to the first channel terminal group, and the second integrated circuit apparatus is able to output a transmission signal to channels that are connected to the second channel terminal group. The arrangement pitch of the channels is thereby smaller than the arrangement pitch of the transmission circuits, enabling an ultrasonic transducer element array having a smaller element pitch to be realized.

Also, in an aspect of the invention, the first integrated circuit apparatus may be flip chip mounted on the first flexible substrate, and the second integrated circuit apparatus may be flip chip mounted on the second flexible substrate.

According to this configuration, rather than mounting integrated circuit apparatuses on a rigid board using a flat package or the like, the integrated circuit apparatuses can be mounted on a flexible substrate, thus enabling the ultrasonic measurement apparatus to be miniaturized.

Also, in an aspect of the invention, the channels may include 1st to mth element groups (where m is a natural number of 2 or more), the plurality of ultrasonic transducer elements included in each of the 1st to mth element groups may be electrically connected in parallel within the element group, and the 1st to mth element groups may be electrically connected in series.

According to this configuration, because the 1st to mth element groups are connected in series, the amplitudes of the reception voltages of the 1st to mth element groups are added together, enabling reception sensitivity to be improved. Also, transmission sound pressure can be increased as a result of the ultrasonic transducer elements of each element group being connected in parallel. This enables an increase in transmission sound pressure to be achieved together with an improvement in reception sensitivity.

Also, in an aspect of the invention, the channels may include 1st to mth element groups (where m is a natural number of 2 or more), the plurality of ultrasonic transducer elements included in each of the 1st to mth element groups may be electrically connected in series within the element group, and the 1st to mth element groups may be electrically connected in parallel.

According to this configuration, because the plurality of ultrasonic transducer elements in each element group are connected in series, the amplitudes of the reception voltages of the plurality of ultrasonic transducer elements are added together, enabling reception sensitivity to be improved. Also, transmission sound pressure can be increased as a result of the 1st to mth element groups being connected in parallel. This enables an increase in transmission sound pressure to be achieved together with an improvement in reception sensitivity.

Also, in an aspect of the invention, the first flexible substrate may have a plurality of openings arranged in an array, the ultrasonic transducer element array may have an ultrasonic transducer element for each of the plurality of openings, the ultrasonic transducer elements may each include a vibration film that closes a corresponding opening among the plurality of openings, and a piezoelectric element part that is provided on the vibration film, and the piezoelectric element part may include a lower electrode that is provided on the vibration film, a piezoelectric layer that is provided so as to cover at least a portion of the lower electrode, and an upper electrode that is provided so as to cover at least a portion of the piezoelectric layer.

According to this configuration, the ultrasonic transducer element array can be configured by ultrasonic transducer elements that use a piezoelectric layer to vibrate a vibration film which closes an opening. This enables the ultrasonic transducer elements to be driven with a drive signal of a lower voltage compared with the case where bulk piezoelectric elements are used, and an integrated circuit apparatus can be manufactured with a process having a low breakdown voltage, thus enabling the integrated circuit apparatus to be formed compactly.

A further aspect of the invention relates to an ultrasonic head unit including the ultrasonic measurement apparatus according to any of the above.

A still further aspect of the invention relates to an ultrasonic probe including the ultrasonic measurement apparatus according to any of the above.

A still further aspect of the invention relates to an ultrasonic imaging apparatus including the ultrasonic probe described above and a display part that displays image data for display.

BRIEF DESCRIPTION OF THE DRAWINGS

The invention will be described with reference to the accompanying drawings, wherein like numbers reference like elements.

FIG. 2A shows exemplary specifications of an ultrasonic probe and diseases, and FIG. 2B shows exemplary specifications of a typical commercial probe.

FIG. 10 shows an illustrative diagram regarding transmission control.

FIGS. 19A to 19C show a detailed exemplary configuration of an ultrasonic head unit.

DESCRIPTION OF EXEMPLARY EMBODIMENTS

Hereinafter, preferred embodiments of the invention will be described in detail. Note that the embodiments described below are not intended to unduly limit the scope of the invention as defined in the claims, and not all combinations of the features described in the embodiments are essential to means for solving the problems addressed by the invention.

1. Comparative Example of the Present Embodiment

As described above, since an IC having a high breakdown voltage is needed when bulk ultrasonic transducer elements are used, there is a problem in that device miniaturization is not readily achieved. For example, although there is a demand, with portable ultrasonic imaging apparatuses, to miniaturize the probe and the device body, miniaturization is hindered when ICs having a high breakdown voltage are mounted.

Also, in JP-A-2005-341085 discussed above, the electrodes of bulk piezoelectric members, which are ultrasonic transducer elements, are connected to a transmission/reception part via a flexible substrate. Since only the wiring that connects the transmission/reception part to the electrodes is formed in the flexible substrate, there is a problem in that the number of components and costs increase.

Also, since almost all ICs (integrated circuit apparatuses) that drive ultrasonic transducer elements are mounted on the main substrate, which consists of a rigid board, ICs are assumed to be constituted by a flat package, and the ICs thus occupy a large area on the main substrate. Also, since a semiconductor process that can withstand a high voltage of around 100 V needs to be used in order to drive a bulk piezoelectric member, a large IC mounting area is required. Thus, with the technique disclosed in JP-A-2005-341085, there is a problem in that device miniaturization is difficult to achieve in the case where this technique is applied to a portable ultrasonic imaging apparatus or the like.

Also, since the area and number of drive ICs will be reduced by reducing the number of drive channels in order to achieve device miniaturization using ICs having a large mounting area such as described above, there is a problem in that the number of channels of the ultrasonic transducer element array decreases. Since the convergence of the ultrasonic beam drops when the number of channels decreases, resolution, which is an important characteristic of an ultrasonic imaging apparatus, will be reduced.

Figure 1A:
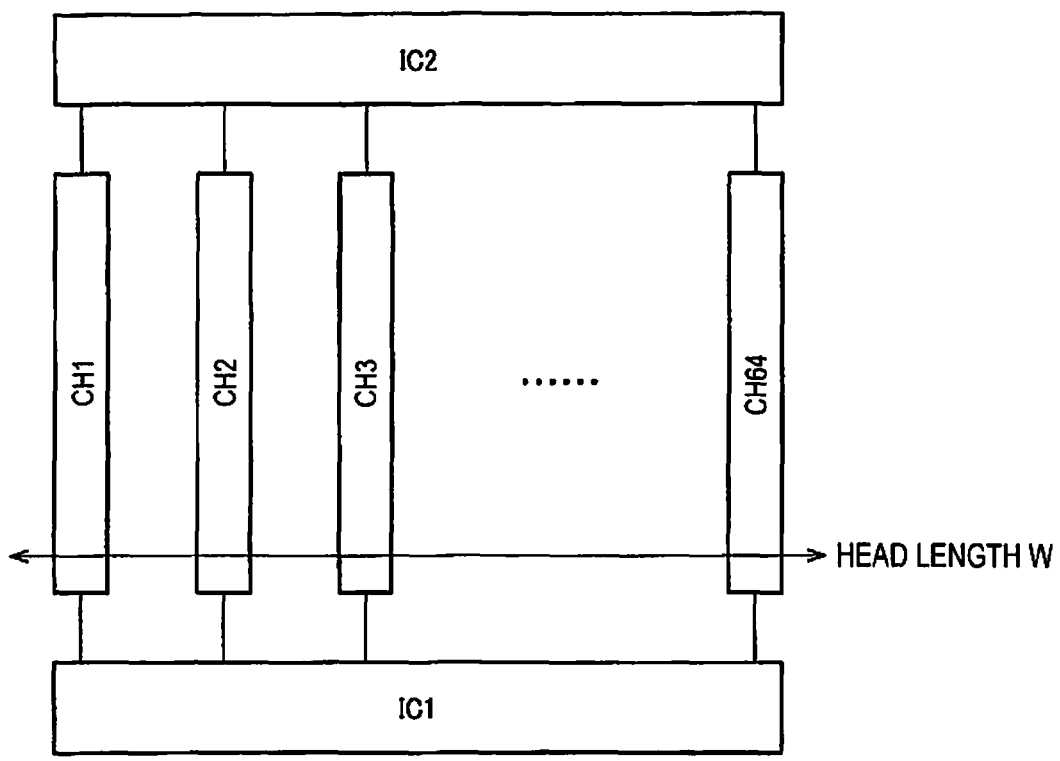
FIGS. 1A and 1B show illustrative diagrams regarding a comparative example of an embodiment of the invention.

In view of this, in the present embodiment, the ultrasonic transducer elements are constituted using thin film piezoelectric elements (piezoelectric layer 30), as will be discussed later with FIG. 3A and the like. With this configuration, the drive ICs can be miniaturized because of being able to drive the ultrasonic transducer elements with 10 to 30 V. For example, an exemplary comparative configuration of the present embodiment is shown in FIG. 1A.

This exemplary comparative configuration includes channels CH1 to CH64 and integrated circuit apparatuses IC1 and IC2 that drive the channels CH1 to CH64 from both ends. The channels CH1 to CH64 are constituted by a plurality of ultrasonic transducer elements, and are, for example, element columns such as will be discussed later with FIG. 5A. The ultrasonic transducer element array is constituted by the channels CH1 to CH64, and the length thereof in the scan direction is given as head length W. Integrated circuit apparatuses IC1 and IC2 are arranged so that the long-side direction thereof coincides with the direction of the head length W, and output terminals for the 64 channels are aligned along the long side thereof. In the present embodiment, since the drive voltage is lower than a bulk piezoelectric member, it is possible to miniaturize the integrated circuit apparatuses IC1 and IC2 to achieve a configuration such as shown in FIG. 1A.

FIG. 2A shows exemplary specifications and diseases given in the present embodiment, and FIG. 2B shows exemplary specifications of a common commercial probe. The suitable depth for observation varies according to the type of disease being diagnosed, and the ultrasonic wave frequency and the number of channels are set according to the depth. For example, the suitable depth for observation and the ultrasonic wave frequency are defined for lymphedema, decubitus and the like shown in FIG. 2A. As shown in FIG. 2B, the head length, number of channels and the like are defined in correspondence to the ultrasonic wave frequency that is determined. Generally, a higher frequency and larger number of channels is required the shallower the depth.

Figure 1B:
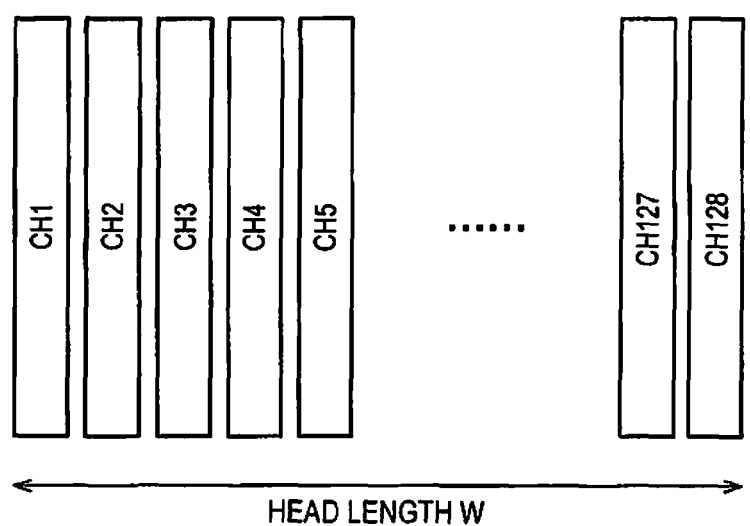

On the other hand, as shown in FIGS. 2A and 2B, the head length is the same (or substantially the same) irrespective of the disease, number of channels, or the like. That is, an increase in the number of channels is required in order to cope with a disease having a shallow observation depth, but the head length will remain unchanged. For example, as shown in FIG. 1B, 128 channels are constituted with the same head length W as in the case of 64 channels. In this case, the integrated circuit apparatuses IC1 and IC2 need to be set to 128 channels, although the use of a process having a breakdown voltage of 10 to 30 V makes it difficult to increase the number of channels while maintaining the length in the long-side direction. Thus, there is a problem in that the length in the long-side direction will be greater than the head length W, making compact arrangement and wiring difficult.

2. Ultrasonic Transducer Element

Hereinafter, an ultrasonic measurement apparatus of the present embodiment that can solve such problems will be described. First, the ultrasonic transducer element that is applied to the ultrasonic measurement apparatus of the present embodiment will be described.

Figure 3A:
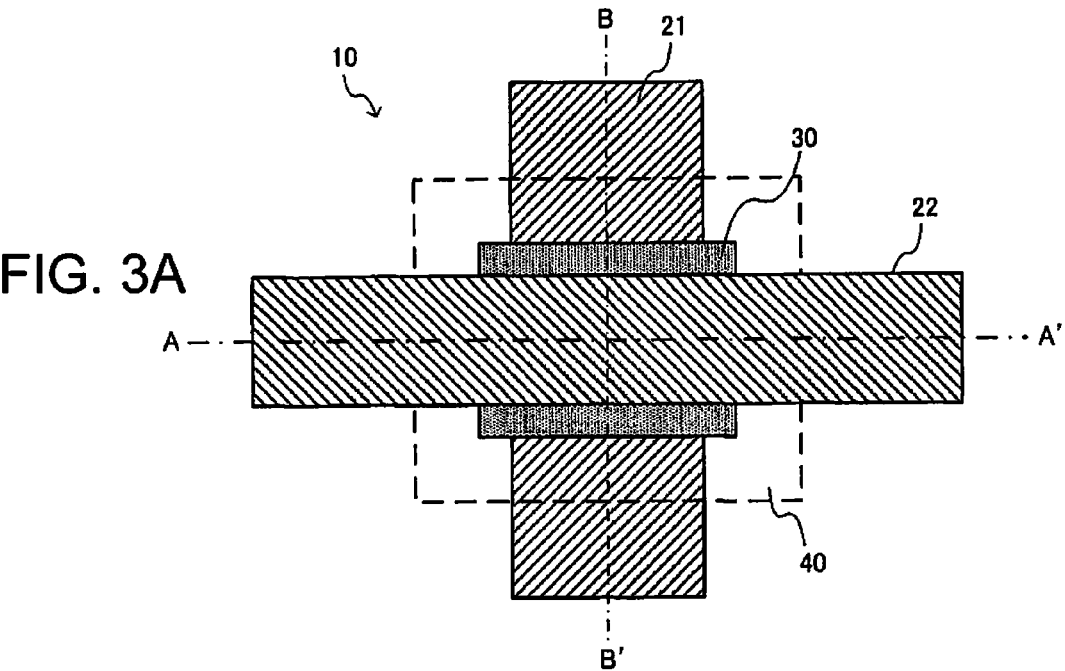
FIGS. 3A to 3C show an exemplary configuration of an ultrasonic transducer element.
Figure 3B:
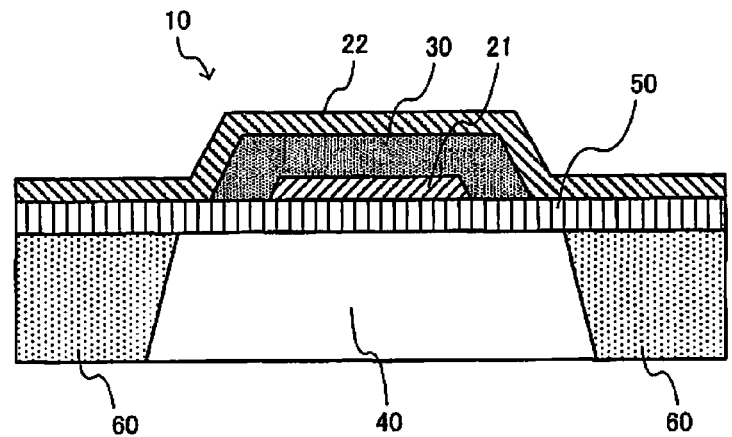
Figure 3C:
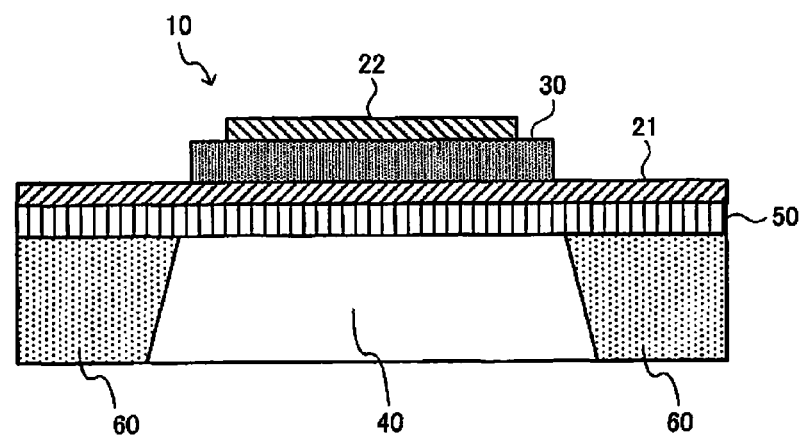

FIGS. 3A to 3C show an exemplary configuration of an ultrasonic transducer element 10 that is applied to an ultrasonic transducer device of the present embodiment. This ultrasonic transducer element 10 includes a vibration film 50 (membrane, supporting member), a first electrode layer 21 (lower electrode layer), a piezoelectric layer 30 (piezoelectric film), and a second electrode layer 22 (upper electrode layer).

The ultrasonic transducer element 10 is formed on a substrate 60. The substrate 60 is a silicon substrate, for example. FIG. 3A is a plan view of the ultrasonic transducer element 10 looking from a direction perpendicular to the element formation side of the substrate 60. FIG. 3B is a cross-sectional view showing a cross-section along AA' in FIG. 3A. FIG. 3C is a cross-sectional view showing a cross-section along BB' of FIG. 3A.

The first electrode layer 21 is formed on an upper layer of the vibration film 50 with a metal thin film, for example. This first electrode layer 21 may be wiring that extends to outside the element formation area as shown in FIG. 3A, and is connected to an adjacent ultrasonic transducer element 10.

The piezoelectric layer 30 is formed using a PZT (lead zirconate titanate) thin film, for example, and is provided so as to cover at least a portion of the first electrode layer 21. Note that the material of the piezoelectric layer 30 is not limited to PZT, and materials such as lead titanate ($PbTiO_3$), lead zirconate ($PbZrO_3$) and lead lanthanum titanate (($Pb$, $La$)$TiO_3$), for example, may be used.

The second electrode layer 22 is formed with a metal thin film, for example, and is provided so as to cover at least a portion of piezoelectric layer 30. This second electrode layer 22 may be wiring that extends to outside the element formation area as shown in FIG. 3A, and is connected to an adjacent ultrasonic transducer element 10.

One of the portion of the first electrode layer 21 covered by the piezoelectric layer 30 and the portion of the second electrode layer 22 covering the piezoelectric layer 30 constitutes a first electrode and the other thereof constitutes a second electrode. The piezoelectric layer 30 is provided so as to be sandwiched by the first electrode and second electrode. The first electrode, the second electrode and the piezoelectric layer 30 are also called piezoelectric element parts.

The vibration film 50 is provided so as to close an opening 40 using a two layer structure consisting of an $SiO_2$ thin film and an $ZrO_2$ thin film, for example. This vibration film 50 supports the piezoelectric layer 30, the first electrode layer 21 and the second electrode layer 22, and is able to produce ultrasonic waves by vibrating in accordance with the expansion and contraction of the piezoelectric layer 30.

The opening 40 (cavity area) is formed by etching using reactive ion etching (RIE) or the like from the bottom surface of the substrate 60 (surface on which the element is not provided). The resonance frequency of the ultrasonic waves is determined by the size of the vibration film 50 which can vibrate due to formation of the opening 40, and the ultrasonic waves are irradiated to the piezoelectric layer 30 side (in a direction from far to near on the page in FIG. 3A).

The piezoelectric layer 30 expands and contracts in an in-plane direction as a result of a voltage being applied between the first electrode and the second electrode, that is, between the first electrode layer 21 and the second electrode layer 22. The ultrasonic transducer element 10 uses a monomorph (unimorph) structure in which a thin piezoelectric element (piezoelectric layer 30) and a metal plate (vibration film 50) are stuck together, and warping occurs because the dimensions of the vibration film 50 remain the same when the piezoelectric layer 30 stuck thereto expands and contracts in-plane. The vibration film 50 vibrates in the film thickness direction as a result of an AC voltage being applied to the piezoelectric layer 30, and ultrasonic waves are irradiated due to the vibrations of the vibration film 50. The voltage applied to the piezoelectric layer 30 is 10 to 30 V, for example, and the frequency is 1 to 10 MHz, for example.

By constituting the ultrasonic transducer element 10 as described above, the element can be miniaturized compared with a bulk ultrasonic transducer element, enabling the element pitch to be reduced. The occurrence of grating lobes can thereby be suppressed. Also, since the element can be driven with a small voltage amplitude compared with a bulk ultrasonic transducer element, the drive circuit can be constituted by circuit elements having a low breakdown voltage.

3. Ultrasonic Transducer Device

Figure 4:
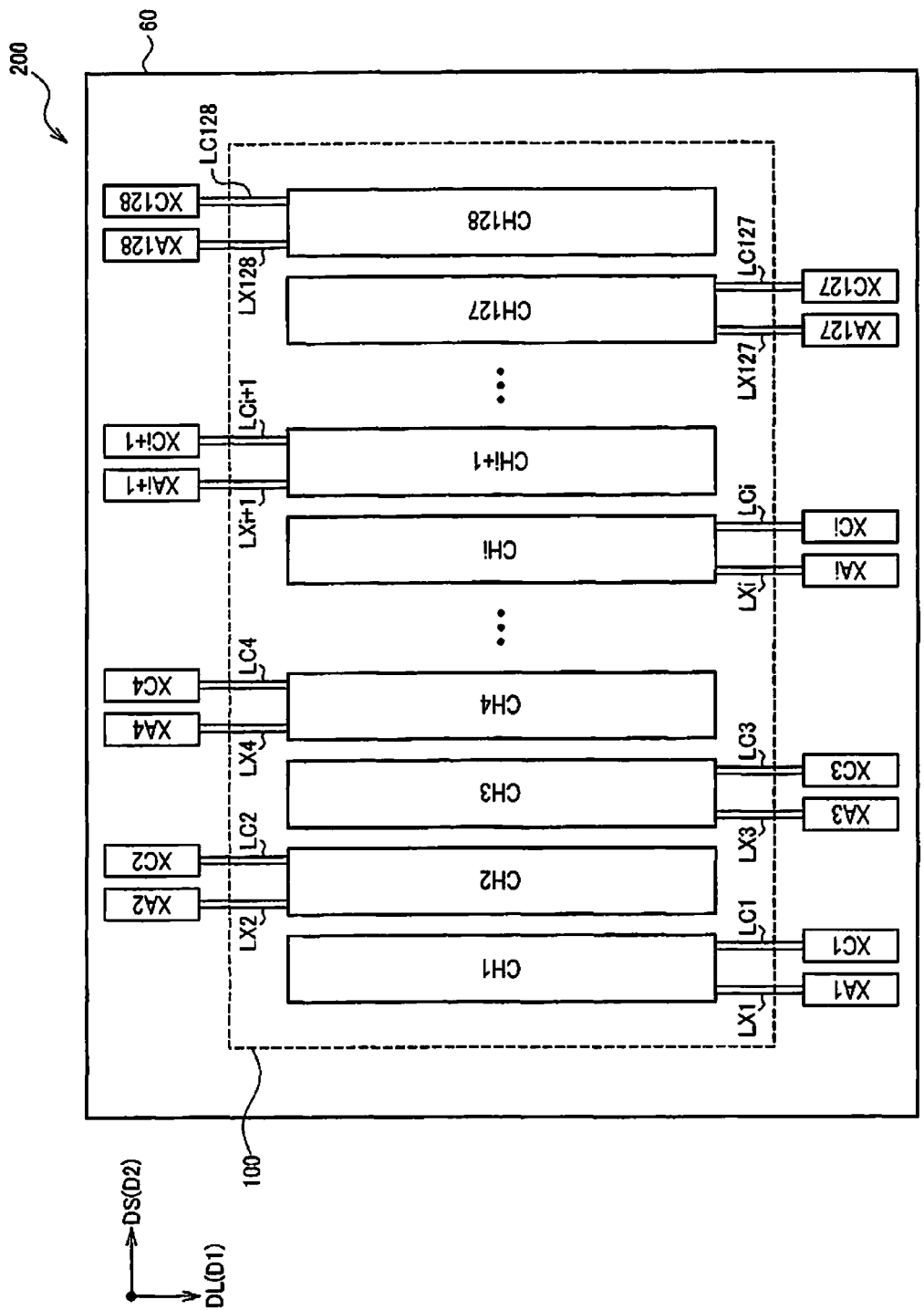
FIG. 4 shows an exemplary configuration of an ultrasonic transducer device.

FIG. 4 shows an exemplary configuration of an ultrasonic transducer device 200 that is included in the ultrasonic measurement apparatus of the present embodiment.

Note that although a case in which a type of transducer that uses a piezoelectric element (thin film piezoelectric element) such as described above as the ultrasonic transducer device 200 is employed will be described below as an example, the present embodiment is not limited thereto. For example, a type of transducer that uses a capacitive element such as a c-MUT (Capacitive Micro-machined Ultrasonic Transducer) may be employed.

Note that, although a case in which the transmission/reception channels are constituted by channels 1 to 128 will be described hereinafter as an example, the present embodiment is not limited thereto, and the transmission/reception channels may be constituted by channels 1 to N other than N=128. Also, although a case in which an element group is connected between a channel terminal (signal terminal) and a common terminal will be described hereinafter as an example, the present embodiment is not limited thereto. That is, the element group may be connected between two signal terminals, and anti-phase signals, for example, may be supplied to these two signal terminals.

The ultrasonic transducer device 200 includes the substrate 60, an ultrasonic transducer element array 100 formed on the substrate 60, channel terminals XA1 to XA128 (signal terminals) formed on the substrate 60, common terminals XC1 to XC128 (broadly speaking, signal terminals) formed on the substrate 60, signal electrode lines LX1 to LX128 formed on the substrate 60, and common electrode lines LC1 to LC128 (broadly speaking, signal electrode lines) formed on the substrate 60.

Channel terminals XAi (where i is an odd number) and common terminals XCi are arranged on one edge portion of the ultrasonic transducer element array 100 in a slice direction DL. The channel terminals XAi are connected to one end of signal electrode lines LXi, and the common terminals XCi are connected to one end of common electrode lines LCi. Channel terminals XAi+1 (where i+1 is an even number) and common terminals XCi+1 are arranged on the other edge portion of the ultrasonic transducer element array 100 in the slice direction DL. The channel terminals XAi+1 are connected to one end of signal electrode lines LXi+1, and the common terminals XCi+1 are connected to one end of common electrode lines LCi+1. For example, the substrate 60 is a rectangle whose long-side direction coincides with a scan direction DS, the odd-numbered channel terminals XAi and common terminals XCi are arranged along one long side of the rectangle, and the even-numbered channel terminals XAi+1 and common terminals XCi+1 are arranged along the other long side of the rectangle.

Here, the slice direction DL (first direction) and the scan direction DS (second direction) represent the directions of the plane of the substrate 60. The scan direction DS corresponds to a direction in which an ultrasonic beam is scanned in a scanning operation such as linear scanning or sector scanning, for example. The slice direction DL is a direction intersecting (for example, orthogonal to) the scan direction DS, and, in the case where, for example, a tomographic image is obtained by scanning an ultrasonic beam, corresponds to a direction orthogonal to the image.

The ultrasonic transducer element array 100 includes channels CH1 to CH128 that are arranged in the scan direction DS. Channels CHi and CHi+1 are each constituted by a plurality of ultrasonic transducer elements 10 that are electrically connected, and are respectively connected to the other end of the signal electrode lines LXi and LXi+1 and the other end of the common electrode lines LCi and LCi+1. The configuration of the channels CHi and CHi+1 will be discussed in detail later.

Transmission and reception of ultrasonic waves are performed as follows. Taking the odd-numbered channels as an example, upon a transmission signal (for example, a voltage pulse) being supplied to the channel terminals XAi, the ultrasonic transducer elements 10 of the channels CHi convert the transmission signal into an ultrasonic wave, and the ultrasonic wave is emitted. The ultrasonic transducer elements 10 then convert an ultrasonic echo reflected by the subject into a reception signal (for example, a voltage signal), and the reception signal is output from the channel terminals XAi. Note that a common voltage (for example, a fixed voltage) is supplied to the common terminals XCi.

4. Channels

Figure 5A:
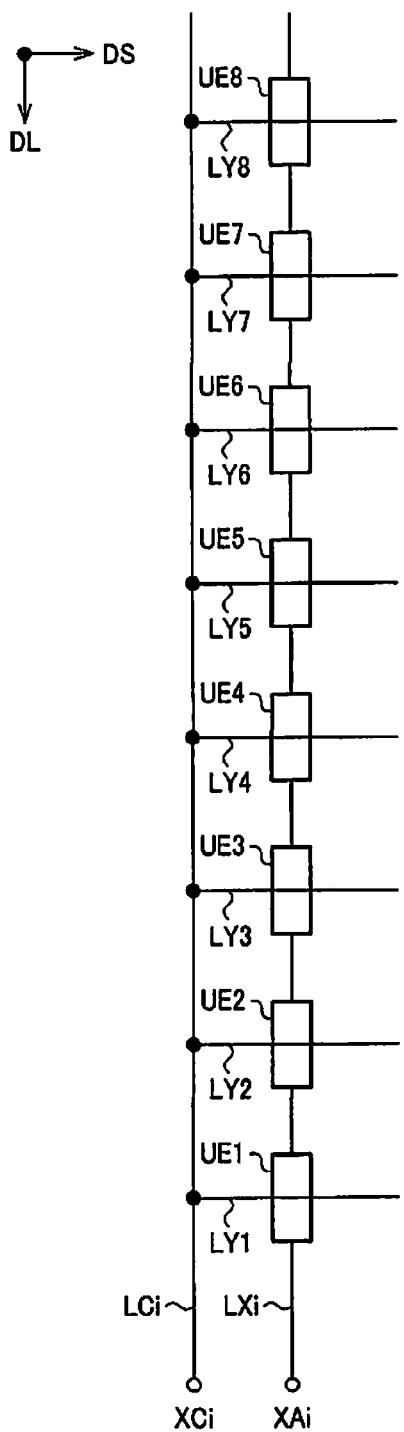
FIGS. 5A and 5B show exemplary configurations of a channel.

A detailed exemplary configuration of the channel CHi (channel element group) is shown in FIG. 5A. Note that the channel CHi+1 can also be similarly constituted.

The channel CHi includes the ultrasonic transducer elements UE1 to UE8 that are arranged in the slice direction DL. One of the electrodes (for example, the first electrode layer 21 in FIG. 3A) of the ultrasonic transducer elements UE1 to UE8 is connected to the signal electrode line LXi. The other electrode (for example, the second electrode layer 22 in FIG. 3A) is connected to common electrode lines LY1 to LY8. The common electrode lines LY1 to LY8 are laid out in the scan direction DS, and are connected to the common electrode line LCi.

In the case where the channel CHi in FIG. 5A is applied to FIG. 4, the ultrasonic transducer elements 10 will be arranged in the ultrasonic transducer element array 100 in a matrix consisting of 8 rows and 128 columns.

Note that although the case where eight ultrasonic transducer elements are arranged in the slice direction DL was described above as an example, the present embodiment is not limited thereto, and M ultrasonic transducer elements (where M is a natural number of 2 or more) other than M=8 may be arranged. That is, the ultrasonic transducer element array 100 may be a matrix consisting of M rows and N columns. Also, the ultrasonic transducer element array 100 is not limited to arrangement in matrix form. For example, channels having different numbers of elements in the slice direction DL may be provided together, or elements may be arranged so as to not be in a straight line in the scan direction DS or the slice direction DL (for example, arranged in a staggered pattern).

Figure 5B:
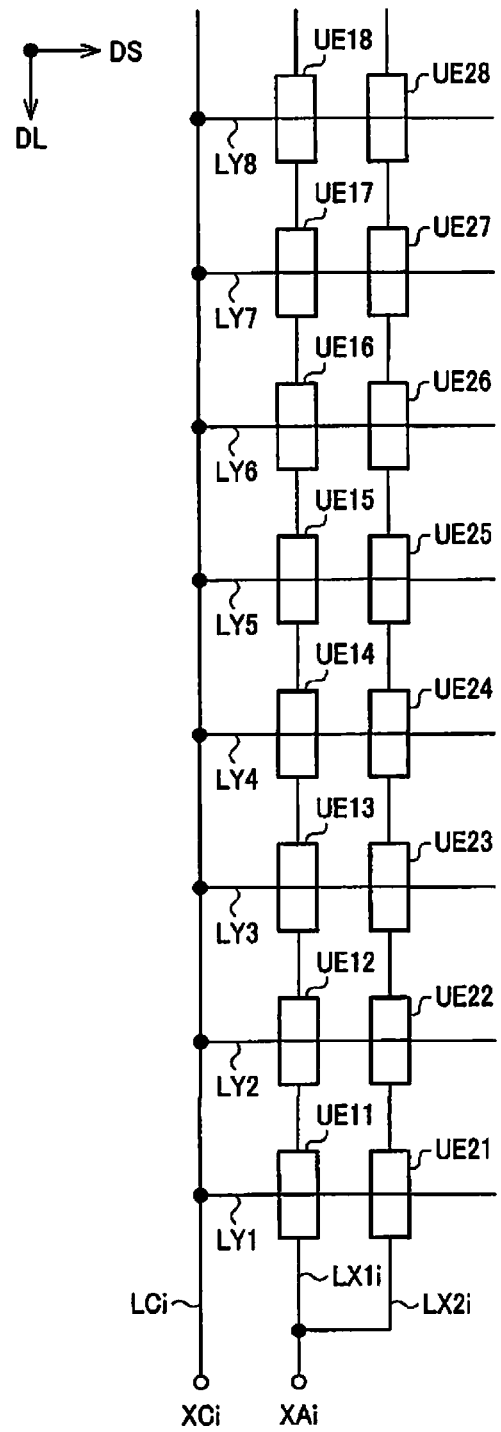

Also, although the case where one channel is constituted by one element column was described above as an example, the present embodiment is not limited thereto, and one channel may be constituted by a plurality of element columns. For example, as shown in FIG. 5B, the channel CHi has ultrasonic transducer elements UE11 to UE18 and UE21 to UE28 arranged in the slice direction DL. The ultrasonic transducer elements UE11 to UE18 and UE21 to UE28 are connected to signal electrode lines LX1$i$ and LX2$i$. The signal electrode lines LX1$i$ and LX2$i$ are connected to the channel terminal XAi.

Also, although the case where a common terminal is connected to each channel and the common electrode lines are divided one to each channel was described above as an example, the present embodiment is not limited thereto. For example, the channels CH1 to CH128 may be connected to shared common electrode lines and common terminals.

5. Basic Configuration of Ultrasonic Measurement Apparatus

Figure 6:
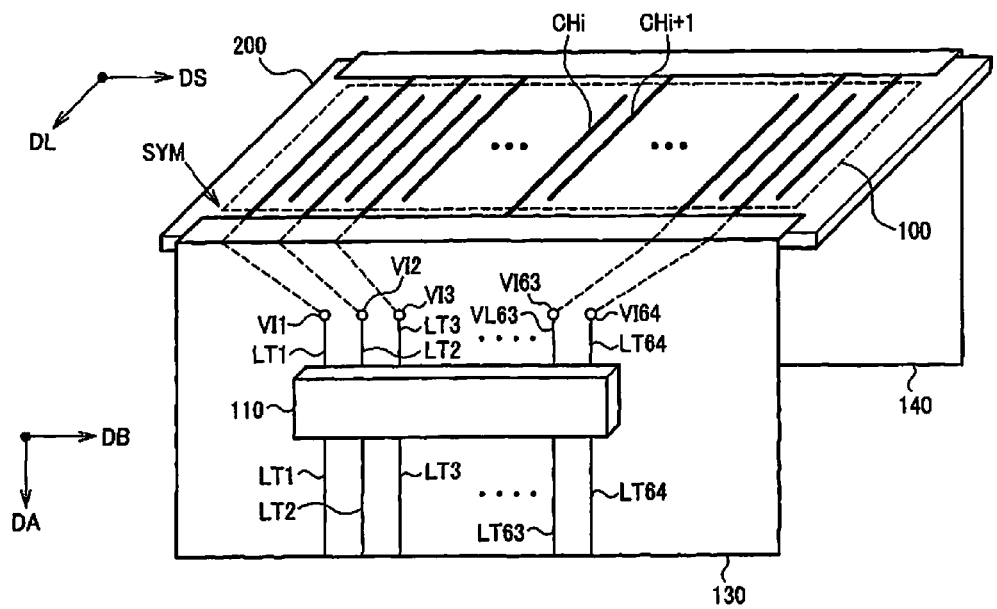
FIG. 6 shows an exemplary basic configuration of an ultrasonic measurement apparatus.
Figure 7:
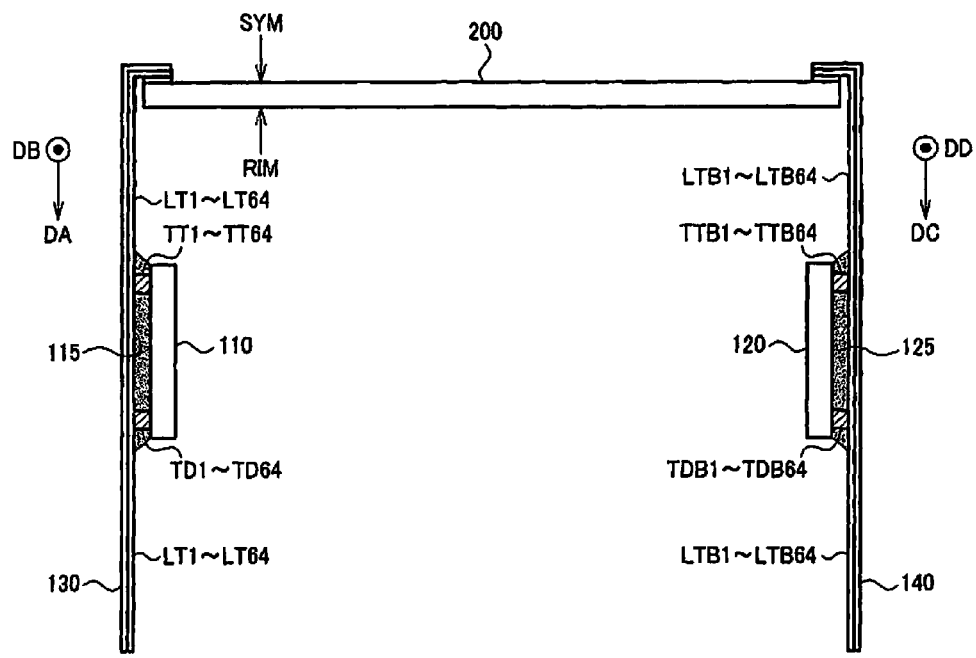
FIG. 7 shows an exemplary basic configuration of an ultrasonic measurement apparatus.

FIGS. 6 and 7 show an exemplary basic configuration of the ultrasonic measurement apparatus of the present embodiment. This ultrasonic measurement apparatus includes the ultrasonic transducer device 200, a first flexible substrate 130, a second flexible substrate 140, a first integrated circuit apparatus 110 that is mounted on the first flexible substrate 130, and a second integrated circuit apparatus 120 that is mounted on the second flexible substrate 140. Note that, hereinafter, the ultrasonic transducer device 200 is also called an element chip as appropriate.

In the flexible substrate 130, signal lines LT1 to LT64 are wired in the direction DA. One end of these signal lines LT1 to LT64 is connected to the odd-numbered channel terminals XA1, XA3, . . . , XA127 of the element chip 200. Here, the directions DA and DB are directions on the flexible substrate 130. The direction DB corresponds to the scanning direction DS of the element chip 200, and is, for example, a direction parallel to the connection end that connects the flexible substrate 130 to the element chip 200, for example. The direction DA intersects (for example, for is orthogonal to) the direction DB.

In a state where the integrated circuit apparatus 110 is mounted, transmission terminals TT1 to TT64 and dummy terminals TD1 to TD64 of the integrated circuit apparatus 110 are connected to the signal lines LT1 to LT64. That is, the transmission terminals TT1 to TT64 will be connected to the odd-numbered channel terminals XA1, XA3, . . . , XA127 of the element chip 200.

The transmission terminals TT1 to TT64 are arrayed along a first long side (HL1 of FIG. 11) of the integrated circuit apparatus 110. The dummy terminals TD1 to TD64 are arrayed along a second long side (HL2) of the integrated circuit apparatus 110. The integrated circuit apparatus 110 is mounted on the flexible substrate 130 such that the long sides lay in the direction DB, and the long side on which the transmission terminal TT1 to TT64 are arrayed faces the ultrasonic transducer device 200 side. In plan view looking at the flexible substrate 130 from the side on which the integrated circuit apparatus 110 is mounted, the signal lines LT1 to LT64 pass under the integrated circuit apparatus 110.

Here, a "dummy terminal" is a terminal that does not input or output signals such as transmission signals, reception signals and control signals, for example, and is, for example, formed from a bump terminal, without a circuit being connected to the bump terminal. Note that the dummy terminals may also include test terminals that input and output signals in a test step of the manufacturing process. Also, an electrostatic protection circuit may be connected to the dummy terminals.

Note that control terminals (TP in FIG. 9) may be arranged along a first short side (HS1) and a second short side (HS2) of the integrated circuit apparatus 110. The control terminals are connected to control signal lines formed on the flexible substrate 130. Transmission pulse signals and transmission/reception control signals are supplied to the control terminals from the transmission/reception control circuit 560 in FIG. 8, for example, and the integrated circuit apparatus 110 generates transmission signals based on these transmission pulse signals and transmission/reception control signals. Also, although not illustrated, common output terminals may be provided in the integrated circuit apparatus 110. The common output terminals supply a common voltage to the common terminals XC1, XC3, . . . , XC127 of the element chip 200.

The terminals of the integrated circuit apparatus 110 are bump terminals, and are formed by metal plating pad terminals of the integrated circuit apparatus 110, for example. Alternatively, a resin layer serving as an insulating layer, metal wiring, and bump terminals that are connected to the metal wiring may be formed on the element formation surface of the integrated circuit apparatus 110.

The channel terminals XA1, XA3, . . . , XA127 of the element chip 200 are formed on a surface SYM on the ultrasonic emission direction side of the element chip 200 (that is, the side on which the piezo-electric object layer 30 is formed). In the example in FIG. 6, one end of the signal lines LT1 to LT64 extends from the outer side (foreside when facing the page) of the flexible substrate 130 to the inner side of the flexible substrate 130 (farside when facing the page) via through holes VI1 to VI64, and is connected to the channel terminals XA1, XA3, . . . , XA127 on the surface SYM on the ultrasonic emission direction side. In this case, the integrated circuit apparatus 110 will be mounted on the outer side of the flexible substrate 130.

In the example in FIG. 7, the signal lines LT1 to LT64 are formed on the inner side of the flexible substrate 130 (on the right side when facing the page), and are connected directly to the channel terminals XA1, XA3, . . . , XA127 of the element chip 200. The integrated circuit apparatus 110 is mounted on the inner side of the flexible substrate 130. Mounting the integrated circuit apparatus 110 on the inner side of the flexible substrate 130 enables the probe head to be mounted more compactly.

The flexible substrate 140 and the integrated circuit apparatus 120 can be constituted similarly to the flexible substrate 130 and the integrated circuit apparatus 110. That is, in the flexible substrate 140, the signal lines LTB1 to LTB64 are wired in the direction DC. One end of the signal lines LTB1 to LTB64 is connected to the even-numbered channel terminals XA2, XA4, . . . , XA128 of the element chip 200. Here, the directions DC and DD are the directions on the flexible substrate 140. The direction DD correspond to the scanning direction DS of the element chip 200, and is, for example, a direction parallel to the connection end connecting the flexible substrate 140 to the element chip 200. The direction DC intersects (for example, is orthogonal to) the direction DD.

In a state where the integrated circuit apparatus 120 is mounted, the transmission terminals TTB1 to TTB64 and the dummy terminals TDB1 to TDB64 of the integrated circuit apparatus 120 are connected to the signal lines LTB1 to LTB64. That is, the transmission terminals TTB1 to TTB64 will be connected to the even-numbered channel terminals XA2, XA4, . . . , XA128 of the element chip 200.

Operations of the above ultrasonic measurement apparatus will now be described. At the time of transmission of ultrasonic waves, transmission signals from the integrated circuit apparatuses 110 and 120 are input to the channel terminals XA1 to XA128 of the ultrasonic transducer device 200 via the transmission terminals TT1 to TT64 and TTB1 to TTB64, and the signal lines LT1 to LT64 and LTB1 to LTB64. The ultrasonic transducer device 200 emits ultrasonic waves using these transmission signals, the ultrasonic waves are reflected from the observation object, and the reflected wave is received by the element chip 200. At the time of reception of this ultrasonic wave, reception signals from the channel terminals XA1 to XA128 are output to a downstream reception circuit (for example, analog front end circuit 550 in FIG. 8A) via the signal lines LT1 to LT64 and LTB1 to LTB64. The circuit configuration and operations of the integrated circuit apparatuses 110 and 120 will be discussed in detail later.

6. Flip Chip Mounting

Hereinafter, flip chip mounting will be described taking the integrated circuit apparatus 110 as an example. Note that the integrated circuit apparatus 120 is also mounted using a similar technique.

Mounting of the integrated circuit apparatus 110 is realized by flip chip mounting (bare chip mounting) using an anisotropic conductive film 115 (ACF), as shown in FIG. 7. The anisotropic conductive film 115 is a resin film containing conductive particles such as metal particulates. When the integrated circuit apparatus 110 has been adhered to the flexible substrate 130 with this anisotropic conductive film 115 interposed therebetween and the anisotropic conductive film 115 has been thermoset, the anisotropic conductive film 115 shrinks on hardening, and the integrated circuit apparatus 110 and the flexible substrate 130 are drawn to each other as a result of the shrinkage. Electrical continuity is then established with the wiring of the flexible substrate 130 by projecting terminals (bumps) of the integrated circuit apparatus 110 crushing the conductive particles, and the integrated circuit apparatus 110 is supported by these projecting terminals countering the shrinkage force due to hardening. In the portions of the film that are not compressed by the terminals, the conductive particles are maintained in an insulated state by the resin, and short-circuiting of the terminals is thereby prevented.

By thus performing flip chip mounting on the flexible substrate 130 using the anisotropic conductive film 115, the mounting area can be reduced compared with the case where the integrated circuit apparatuses of a flat package are mounted to a downstream printed circuit board (rigid board). Also, since the element chip 200 of the present embodiment can be driven at around 10 to 30 V as described above, the integrated circuit apparatus 110 can be miniaturized. Thus, miniaturization by flip chip mounting, which is difficult with bulk piezoelectric elements that required integrated circuit apparatuses having a high breakdown voltage, can be easily realized.

Note that the flip chip mounting is, for example, face-down mounting in which mounting is performed with the element formation surface on the flexible substrate 130 side. Alternatively, the flip chip mounting may be face-up mounting in which mounting is performed with the opposite surface to the element formation surface on the flexible substrate 130 side.

In the present embodiment, the dummy terminals TD1 to TD64 are provided on the integrated circuit apparatus 110. Hypothetically, in the case where the dummy terminals TD1 to TD64 are not provided, only the transmission terminals TT1 to TT64 exist on one long side of the integrated circuit apparatus 110, and the shrinkage force due to hardening of the anisotropic conductive film 115 causes an imbalance between the side with terminals and the side without terminals. Due to this imbalance, a force that draws the integrated circuit apparatus 110 and the flexible substrate 130 together occurs on the side without terminals. On the other hand, a force that lifts up the terminals occurs on the side with terminals due to the drawing force, possibly causing the transmission terminals TT1 to TT64 to rise away from the signal lines LT1 to LT64.

Regarding this point, in the present embodiment, the dummy terminals TD1 to TD64 are provided on the second long side of the integrated circuit apparatus 110. Since the countering force of the transmission terminals TT1 to TT64 and the countering force of the dummy terminals TD1 to TD64 with respect to the shrinkage force due to hardening of the anisotropic conductive film 115 are thereby balanced out, the forces are in equilibrium and electrical continuity between the transmission terminals TT1 to TT64 and signal lines LT1 to LT64 can be maintained.

Note that the present embodiment is not limited to mounting using the anisotropic conductive film 115 (ACF), and the integrated circuit apparatus 110 may be mounted to the flexible substrate 130 using ACP (anisotropic conductive paste), NCF (non-conductive film), NCP (non-conductive paste), or the like, for example.

The second integrated circuit apparatus 120 is also mounted similarly to the above. That is, the integrated circuit apparatus 120 is flip chip mounted on the flexible substrate 140, using an anisotropic conductive film 125.

7. Detailed Configuration of Ultrasonic Measurement Apparatus

Figure 8:
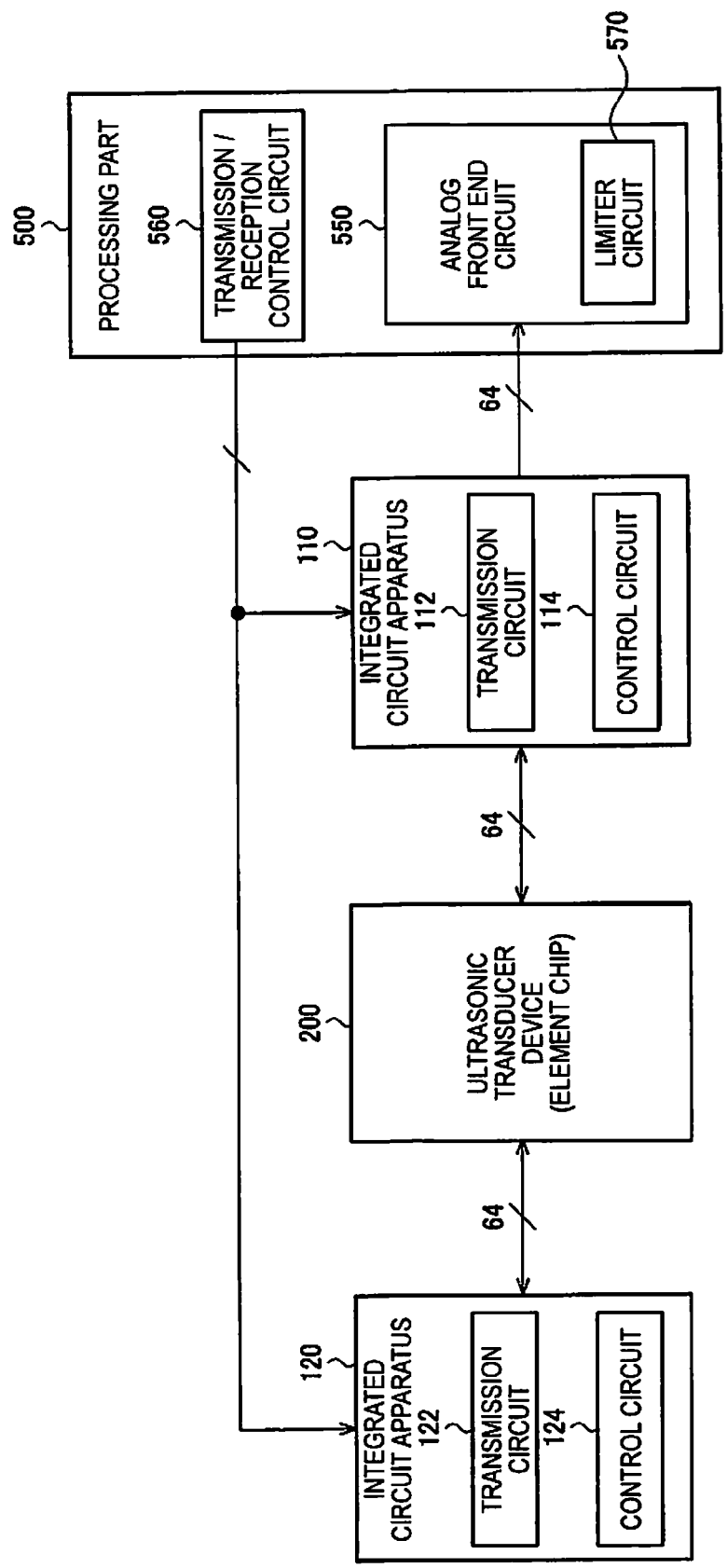
FIG. 8 shows a circuit block diagram of an exemplary configuration of an ultrasonic measurement apparatus.

FIG. 8 shows a circuit block diagram of an exemplary configuration of an ultrasonic measurement apparatus. This ultrasonic measurement apparatus includes the element chip 200, the integrated circuit apparatuses 110 and 120, and a processing part 500. The processing part 500 includes the analog front end circuit 550 and a transmission/reception control circuit 560.

The transmission/reception control circuit 560 performs ultrasonic wave transmission control and reception control on the integrated circuit apparatuses 110 and 120. The transmission/reception control circuit 560 supplies control signals thereof to the integrated circuit apparatuses 110 and 120 via the control terminals (TP in FIG. 9) of the integrated circuit apparatuses 110 and 120.

A reception signal is input to the analog front end circuit 550 from the element chip 200 via the flexible substrates 130 and 140, and the analog front end circuit 550 performs reception processing on the reception signal. Reception processing involves processing such as amplification, A/D conversion and reception focusing, for example. Also, the analog front end circuit 550 includes a limiter circuit 570 that limits the high-voltage transmission signals that are output by the integrated circuit apparatuses 110 and 120. Since the amplitude of the transmission signals is around 10 to 30 V, and the analog front end circuit 550 operates at several volts, the analog front end circuit 550 may be damaged (by electrostatic discharge) when the transmission signals are input directly to the analog front end circuit 550. Thus, the limiter circuit 570 is provided, and input of transmission signals to the analog front end circuit 550 is prevented. Note that, rather than the limiter circuit 570, a switch element that turns off during the transmission period of ultrasonic waves may be provided.

The integrated circuit apparatus 110 includes a transmission circuit 112 that amplifies the transmission pulse signals, and a control circuit 114 that controls the transmission circuit 112 based on instructions from the transmission/reception control circuit 560. The integrated circuit apparatus 120 includes a transmission circuit 122 that amplifies the transmission pulse signals, and a control circuit 124 that controls the transmission circuit 122 based on instructions from the transmission/reception control circuit 560.

Figure 9:
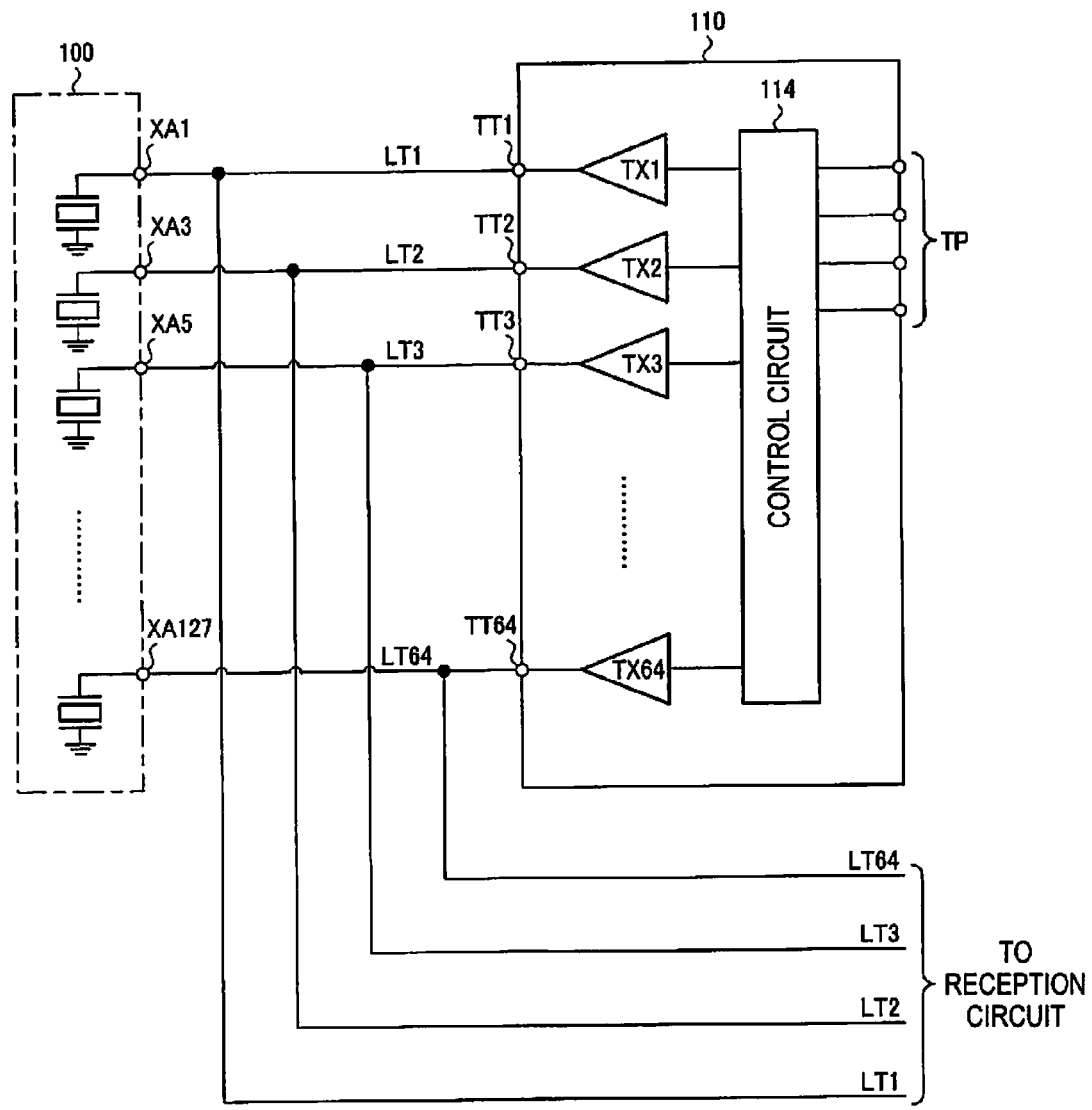
FIG. 9 shows a detailed exemplary configuration of an integrated circuit apparatus.

An detailed exemplary configuration of the integrated circuit apparatus 110 is shown in FIG. 9. Note that although the integrated circuit apparatus 110 is given as an example, the integrated circuit apparatus 120 can be constituted similarly. The integrated circuit apparatus 110 includes transmission circuits TX1 to TX64 (for example, pulsers) and the control circuit 114. The transmission circuits TX1 to TX64 correspond to the transmission circuit 112 in FIG. 8.

During the transmission period of ultrasonic waves, the transmission/reception control circuit 560 inputs transmission control commands to the control circuit 114 via the terminal group TP (control terminals). For example, the transmission control commands are written to a register which is not illustrated. The control circuit 114 performs scanning control and transmission focusing control based on the transmission control commands, and supplies transmission pulse signals to the transmission circuits TX1 to TX64. The transmission circuits TX1 to TX64 amplify the supplied transmission pulse signals, and output the amplified transmission pulse signals to the ultrasonic transducer element array 100 via the transmission terminals TT1 to TT64.

During the reception period of ultrasonic waves, the ultrasonic transducer element array 100 receives the reflected waves of ultrasonic waves reflected from the observation object, and the reception signals thereof are input to the analog front end circuit 550 via signal lines LT1 to LT64. The reception signals, being weak (voltage swing is small) compared with the transmission signals, pass through without being limited by the limiter circuit 570, and are input to the reception circuit (for example, low noise amplifier or A/D conversion circuit) of the analog front end circuit 550, or the like.

8. Transmission/Reception Control

Transmission/reception control will be described in detail, taking the case where linear scanning is performed as an example. FIG. 10 shows an illustrative diagram of transmission control. Although the case where one ultrasonic beam is output with eight channels will hereinafter be described as an example, the present embodiment is not limited thereto.

Scanning periods T1, T2, . . . , shown in FIG. 10 are each a period during which one ultrasonic beam is transmitted and received in a linear scanning. The pulse signals P1 to P8 are the signals of pulse waveforms constituting one ultrasonic beam. A delay is provided in the pulse signals P1 to P8 by transmission focusing control. For example, in the case of emitting an ultrasonic beam in the frontal direction (perpendicular to substrate 60), the outer pulse signals P1 and P8 are emitted first, and the delay increases towards the middle pulse signals P4 and P5.

In the scanning period T1, transmission and reception are performed using the channels CH1 to CH8. That is, the transmission circuits TX1 to TX4 of the integrated circuit apparatus 110 output the odd-numbered pulse signals P1, P3, P5 and P7 to the odd-numbered channels CH1, CH3, CH5 and CH7, and the transmission circuits TX1 to TX4 of the integrated circuit apparatus 120 output the even-numbered pulse signals P2, P4, P6 and P8 to the even-numbered channels CH2, CH4, CH6 and CH8. At the time of reception, the analog front end circuit 550 receives the reception signals of the channels CH1 to CH8, performs delay adjustment according to the delay at the time of transmission, and acquires one reception signal (signal for one line in the depth direction) by adding together the reception signals after delay adjustment.

In the next scanning period T2, the ultrasonic beam is shifted one channel, and transmission and reception are performed using the channels CH2 to CH9. That is, the transmission circuits TX1 to TX4 of the integrated circuit apparatus 120 output the odd-numbered pulse signals P1, P3, P5 and P7 to the even-numbered channels CH2, CH4, CH6 and CH8, and the transmission circuits TX2 to TX5 of the integrated circuit apparatus 110 output the even-numbered pulse signals P2, P4, P6 and P8 to the odd-numbered channels CH3, CH5, CH7 and CH9. The analog front end circuit 550 obtains one reception signal from the reception signals of the channels CH2 to CH9.

In the subsequent scanning periods T3, T4, ..., the ultrasonic beam is shifted one channel, and similar transmission/reception control is performed.

Note that the pulse signals P1 to P8 are not limited to emission of an ultrasonic beam to the front, and may be waveforms having a delay for emitting an ultrasonic beam in a direction diagonal to the front, for example. Also, the pulse signals P1 to P8 do not need to be the same in each scanning period, and may be pulse signals having a different delay in each scanning period, for example. For example, the pulse signals may have a delay that changes the emission direction sequentially in the scanning periods T1, T2, T3, ....

Also, in the present embodiment, the scanning operation is not limited to linear scanning, and sector scanning (phase scanning) may be performed, for example. In the case of performing sector scanning, the beam direction is scanned by phase control of the channels CH1 to CH128. At this time, the phase difference (delay) of the channels CH1 to CH128 is controlled by appropriately controlling the delay of the odd-numbered channels that are assigned to the integrated circuit apparatus 110 and the even-numbered channels that are assigned to the integrated circuit apparatus 120.

9. Layout Configuration of Integrated Circuit Apparatus

Figure 11:
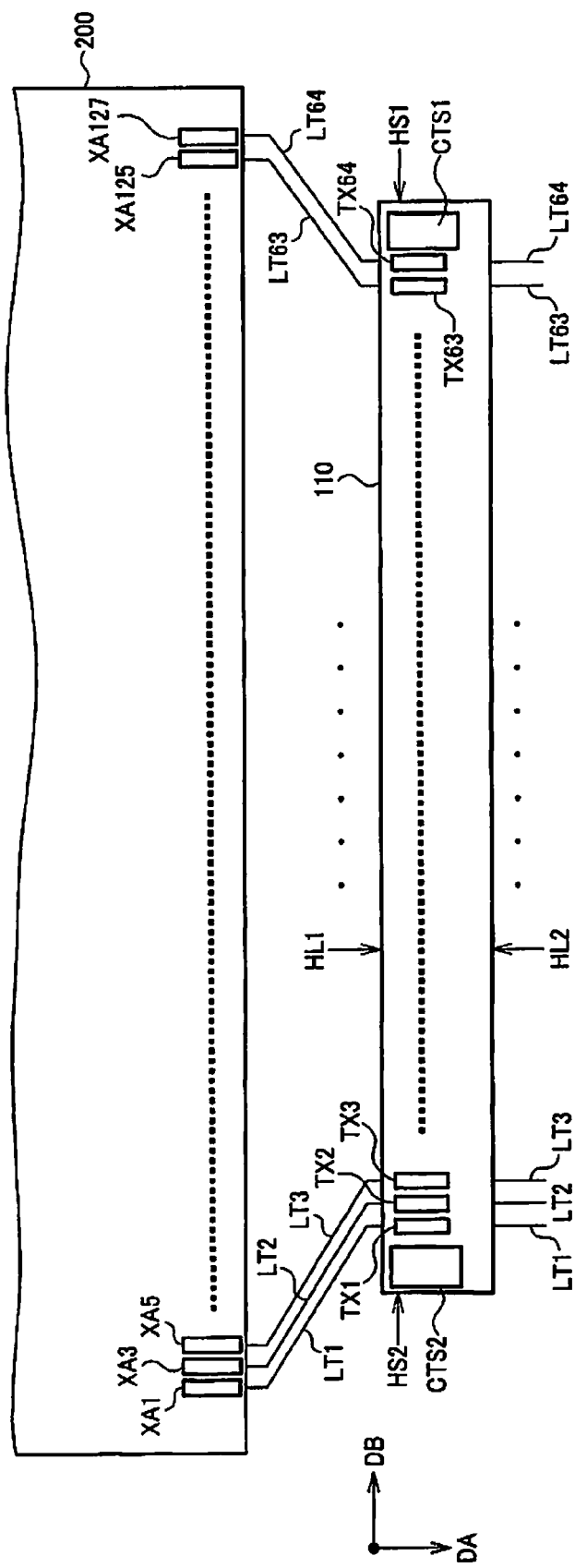
FIG. 11 shows an exemplary layout configuration of an integrated circuit apparatus.

FIG. 11 shows an exemplary layout configuration of the integrated circuit apparatus 110. Note that although the integrated circuit apparatus 110 will be given as an example, the integrated circuit apparatus 120 can also be constituted similarly. The integrated circuit apparatus 110 includes the transmission circuits TX1 to TX64, and the control circuits CTS1 and CTS2.

The transmission circuits TX1 to TX64 are arrayed in the long-side direction of the integrated circuit apparatus 110. Since the integrated circuit apparatus 110 is constituted in a long thin rectangular shape in the long-side direction as a result of adopting such an arrangement, the transmission terminals TT1 to TT64 of the integrated circuit apparatus 110 can be provided opposing the ultrasonic transducer element array 100. The wiring between terminals is thereby simplified, making compact configuration possible with respect to the flexible substrate 130. Note that the long sides of the integrated circuit apparatus 110 are the first long side HL1 and the second long side HL2. The first long side HL1 opposes the channel terminals XA1, XA3, ..., XA127 at the time of mounting, and is the side on which the transmission terminals TT1 to TT64 are arrayed. The second long side HL2 opposes the first long side HL1, and is the side on which the dummy terminals TD1 to TD64 are arrayed.

The control circuit CTS1 is arranged on the first short side HS1 side of the integrated circuit apparatus 110, and the control circuit CTS2 is arranged on the second short side HS2 side of the integrated circuit apparatus 110. The control circuits CTS1 and CTS2 correspond to the control circuit 114 in FIG. 8. By arranging control circuits CTS1 and CTS2 on the short sides in this way, the control terminals can be arranged on the short side, and the short side can be utilized effectively while maintaining the long narrow shape in the long-side direction.

10. Ultrasonic Probe

Figure 12:
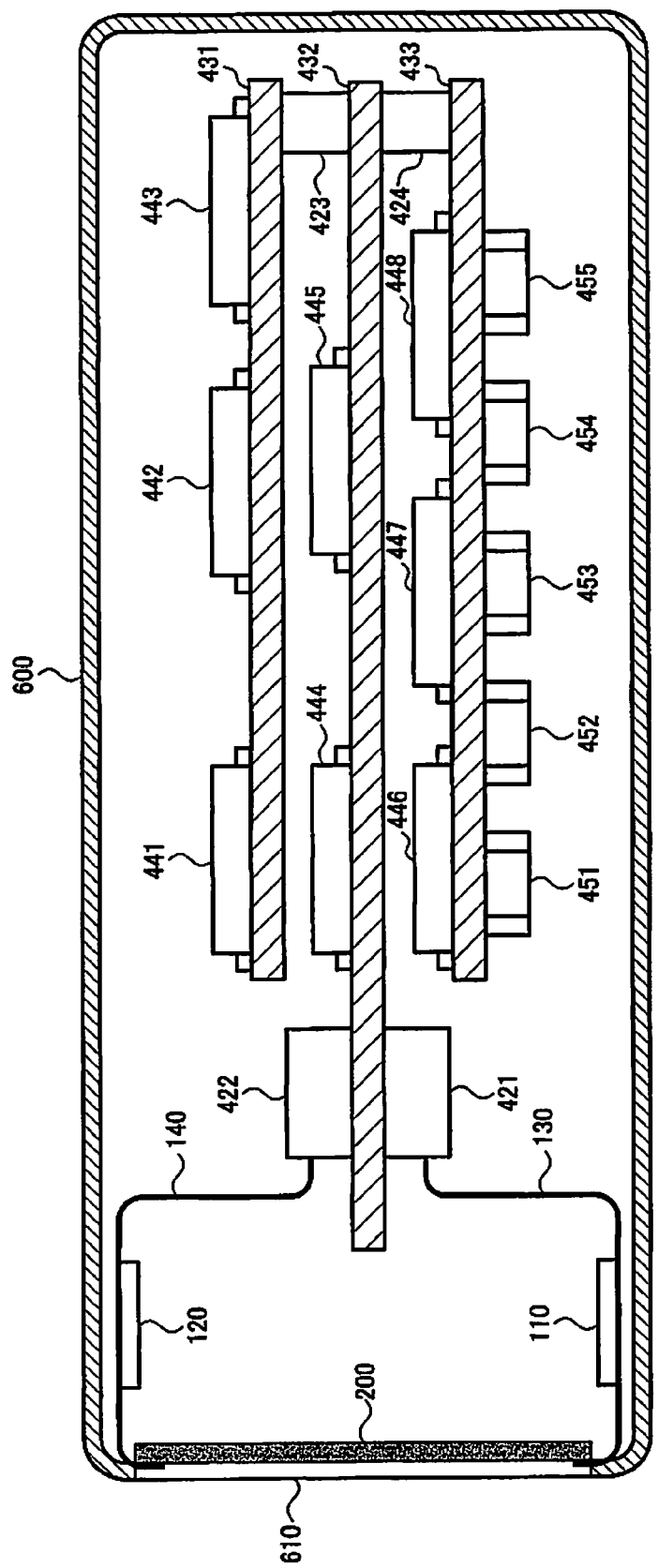
FIG. 12 shows an exemplary configuration of an ultrasonic probe.

FIG. 12 shows an exemplary configuration of a ultrasonic probe that includes the ultrasonic measurement apparatus of the present embodiment. This ultrasonic probe includes a case 600, an acoustic member 610, the element chip 200, the integrated circuit apparatuses 110 and 120, flexible substrates 130 and 140, the connectors 421 to 424, rigid boards 431 to 433, integrated circuit apparatuses 441 to 448, and circuit elements 451 to 455.

The acoustic member 610 is constituted by an acoustic matching layer, an acoustic lens and the like, for example, and performs acoustic impedance matching between the element chip 200 and the observation object, convergence of the ultrasonic beam, and the like. The flexible substrates 130 and 140 on which the integrated circuit apparatuses 110 and 120 are mounted are connected to the rigid board 432 by the connectors 421 and 422. The rigid boards 431 to 433 are connected by the connectors 423 and 424, and the integrated circuit apparatuses 441 to 448 and the circuit elements 451 to 455 are mounted on the rigid boards 431 to 433.

The analog front end circuit 550 and the transmission/reception control circuit 560 that were described with FIG. 8 and the like are included in the integrated circuit apparatuses 441 to 448. Also, the integrated circuit apparatuses 441 to 448 can include, for example, a communication processing circuit that performs communication processing with the main body of the ultrasonic imaging apparatus that connects the ultrasonic probe, an image processing circuit that performs image processing, and the like. Various types of circuit elements such as resistive elements, capacitors, coils, electronic buttons and switches, for example, can be used for the circuit elements 451 to 455.

As described above, a bulk ultrasonic transducer element needs a drive voltage of around 100 V, thus requiring an IC having a high breakdown voltage, and making device miniaturization (for example, miniaturization of the probe) difficult to achieve. In view of this, in the present embodiment, as described with FIG. 1A and the like, thin-film piezoelectric elements are used as ultrasonic transducer elements to reduce the drive voltage to 10 to 30 V, enabling miniaturization to be realized using a drive IC having a low breakdown voltage.

However, there are cases where the arrangement pitch of the channels needs to be reduced, as described with FIG. 1B and the like, and because the size of the drive IC increases with the increase in the number of channels, compact arrangement may not be possible. For example, with the layout of FIG. 11 and the like, the arrangement pitch of the transmission circuits TX1 to TX64 cannot be reduced below a prescribed pitch due to the breakdown voltages, and thus the size of the drive IC may be much greater than the head length W in FIG. 18.

In view of this, the ultrasonic measurement apparatus of the present embodiment includes the ultrasonic transducer device 200, the first channel terminal group (XA1, XA3, . . . , XA127), the second channel terminal group (XA2, XA4, . . . , XA128), the first integrated circuit apparatus 110, and the second integrated circuit apparatus 120 (FIG. 4, FIG. 6, etc.).

The ultrasonic transducer device 200 has the substrate 60 and the ultrasonic transducer element array 100 which is arranged on the substrate 60. The first channel terminal group (XA1, XA3, . . . , XA127) is arranged at one edge portion of the ultrasonic transducer element array 100 in the first direction (slice direction DL). The second channel terminal group (XA2, XA4, . . . , XA128) is arranged at the other edge portion of the ultrasonic transducer element array 100 in the first direction. The first flexible substrate 130 is provided on the one edge portion side and has arranged thereon a first wiring group (LT1 to LT64) that is connected to the first channel terminal group. The first integrated circuit apparatus 110 is mounted on the first flexible substrate 130, and performs at least one of signal transmission to the first channel terminal group and signal reception from the first channel terminal group. The second flexible substrate 140 is provided on the other edge portion side and has arranged thereon a second wiring group (LTB1 to LTB64) that is connected to the second channel terminal group. The second integrated circuit apparatus 120 is mounted on the second flexible substrate 140, and performs at least one of signal transmission to the second channel terminal group and signal reception from the second channel terminal group.

On the ultrasonic transducer element array 100, channels that are connected to the first channel terminal group (XA1, XA3, . . . , XA127), and channels that are connected to the second channel terminal group (XA2, XA4, . . . , XA128) are arranged alternately every channel in the second direction (scanning direction DS) intersecting the first direction.

According to this configuration, the integrated circuit apparatuses 110 and 120 each need only supply a transmission signal every other channel, thus enabling the arrangement pitch of the channels of the ultrasonic transducer element array 100 to be reduced, even without changing the size of the integrated circuit apparatus 110. This configuration thereby realizes a compact arrangement, and can handle various applications such as described with FIG. 2A and the like. Also, since more ultrasonic transducer elements can be mounted on the same area, a higher resolution can be achieved.

Here, channels are ultrasonic transducer elements that are connected to the same channel terminal (i.e., that are supplied with the same transmission signal), among the ultrasonic transducer elements arranged in the ultrasonic transducer element array 100. For example, in the example in FIG. 5A, the ultrasonic transducer elements UE1 to UE8 constitute a channel, whereas in the example in FIG. 16 discussed below, the ultrasonic transducer elements UE11 to UE43 constitute a channel.

Also, in the present embodiment, in the first scanning period T1, the first integrated circuit apparatus 110 outputs the odd-numbered pulse signals P1, P3, P5 and P7, among the 1st to kth pulse signals P1 to P8 (where k=8; k can be a natural number of 2 or more), to the channel terminals XA1, XA3, XA5 and XA7 belonging to the first channel terminal group, among the 1st to kth channel terminals XA1 to XA8, and the second integrated circuit apparatus 120 outputs the even-numbered pulse signals P2, P4, P6 and P8, among the 1st to kth pulse signals P1 to P8, to the channel terminals XA2, XA4, XA6 and XA8 belonging to the second channel terminal group, among the 1st to kth channel terminals XA1 to XA8. In the second scanning period T2 subsequent to the first scanning period T1, the second integrated circuit apparatus 120 outputs the odd-numbered pulse signals P1, P3, P5 and P7, to the channel terminals XA2, XA4, XA6 and XA8 belonging to the second channel terminal group, among the 2nd to k+1th channel terminals XA2 to XA9, and the first integrated circuit apparatus 110 outputs the even-numbered pulse signals P2, P4, P6 and P8 to the channel terminals XA3, XA5, XA7 and XA9 belonging to the first channel terminal group, among the 2nd to k+1th channel terminals XA2 to XA9 (FIG. 10, etc.).

According to this configuration, scanning operations can be realized in the present embodiment in which channels that are connected to the first channel terminal group and channels that are connected to the second channel terminal group are arranged alternately every channel. That is, linear scanning in which the ultrasonic beam is shifted one channel every scanning period can be realized by the integrated circuit apparatuses 110 and 120 outputting even-numbered and odd-numbered pulse signals alternately every scanning period.

Also, in the present embodiment, the ultrasonic measurement apparatus includes the processing part 500 which outputs control commands for controlling transmission in the first scanning period T1 and the second scanning period T2 to the first integrated circuit apparatus 110 and the second integrated circuit apparatus 120 (FIG. 8, etc.). The first integrated circuit apparatus 110 and the second integrated circuit apparatus 120 each have a plurality of transmission circuits TX1 to TX64 that transmit the pulse signals P1 to P8, and a control circuit 114 or 124 that controls the plurality of transmission circuits based on the control commands (FIG. 9, etc.).

Providing such control commands enables the integrated circuit apparatuses 110 and 120 to be instructed to perform scanning operations such as described above. That is, the transmission circuits TX1 to TX64 are able to transmit appropriate pulse signals P1 to P8 as a result of the processing part 500 outputting control commands, and the control circuits 114 and 124 interpreting the control commands and setting the pulse signal delay and the output channels.

Also, in the present embodiment, the processing part 500 performs reception processing of reception signals. That is, the processing part 500 performs reception processing based on the reception signals from the first channel terminal group (XA1, XA3, . . . , XA127) and the reception signals from the second channel terminal group (XA2, XA4, . . . , XA128) obtained by the first integrated circuit apparatus 110 and the second integrated circuit apparatus 120 transmitting signals (FIG. 8, etc.).

In the reception processing, it is necessary to combine the reception signals of a plurality of channels by processing such as reception focusing, and obtain a final reception signal. Regarding this point, in the present embodiment, the integrated circuit apparatuses 110 and 120 respectively transmit signals to odd-numbered and even-numbered channels, and a final reception signal can be acquired by the processing part 500 performing reception processing on the reception signals of the odd-numbered and even-numbered channels in the reception.

Also, in the present embodiment, the 1st to Nth channels CH1 to CH128 (where N=128; N can be a natural number of 2 or more) are arranged in the ultrasonic transducer element array 100 in the second direction (scan direction DS). The first channel terminal group (XA1, XA3, . . . , XA127) is connected to the odd-numbered channels CH1, CH3, . . . , CH127, among the 1st to Nth channels. The second channel terminal group (XA2, XA4, . . . , XA128) is connected to the even-numbered channel CH2, CH4, . . . , CH128, among the 1st to Nth channel.

According to this configuration, channels that are connected to the first channel terminal group (XA1, XA3, . . . , XA127) and channels that are connected to the second channel terminal group (XA2, XA4, . . . , XA128) can be arranged alternately every channel.

Also, in the present embodiment, the first integrated circuit apparatus 110 is mounted such that the long-side direction of the first integrated circuit apparatus 110 coincides with a third direction DB that is a direction coinciding with the edge connecting the first flexible substrate 130 to the 1st channel terminal group XA1, XA3, . . . , XA127. The second integrated circuit apparatus 120 is mounted such that the long-side direction of the second integrated circuit apparatus 120 coincides with a fourth direction DD that is a direction coinciding with the edge connecting the second flexible substrate 140 to the second channel terminal group XA2, XA4, . . . , XA128 (FIG. 6, FIG. 7, etc.).

Also, in the present embodiment, the plurality of transmitting circuits TX1 to TX64 of the first integrated circuit apparatus 110 are arranged in the third direction DB (FIG. 11, etc.), and transmit signals to the first channel terminal group (XA1, XA3, . . . , XA127). The plurality of transmitting circuits TX1 to TX64 of the second integrated circuit apparatus 120 are arranged in the fourth direction DD, and transmit signals to the second channel terminal group (XA2, XA4, . . . , XA128).

According to this configuration, the integrated circuit apparatuses 110 and 120 can be arranged so as to oppose the ultrasonic transducer element array 100, enabling a compact arrangement and simple wiring to be realized. Also, the first integrated circuit apparatus 110 is able to output a transmission signal to the odd-numbered channels, and the second integrated circuit apparatus 120 is able to output a transmission signal to the even-numbered channels. The number of transmission circuits aligned in the directions DB and DD corresponding to the scanning direction DS can thereby be reduced to half the number of channels, enabling an ultrasonic transducer element array 100 having a smaller element pitch to be realized, even with the integrated circuit apparatuses 110 and 120 of the same size.

Also, in the present embodiment, the first integrated circuit apparatus 110 is flip chip mounted to the first flexible substrate 130, and the second integrated circuit apparatus 120 is flip chip mounted to the second flexible substrate 140.

According to this configuration, rather than the integrated circuit apparatuses being mounted on a rigid board using a flat package or the like, for example, the integrated circuit apparatuses 110 and 120 can be mounted on the first flexible substrate 130 and the second flexible substrate 140 respectively, thus enabling the ultrasonic measurement apparatus to be miniaturized.

11. Second Detailed Configuration of Ultrasonic Measurement Apparatus

In the abovementioned embodiment, the case where the integrated circuit apparatus 110 includes only the transmission circuits TX1 to TX64 and the control circuit 114 was described as an example, but the present embodiment is not limited thereto, and the integrated circuit apparatus 110 may also further include switch elements, multiplexers and the like. Hereinafter, an exemplary configuration of an ultrasonic measurement apparatus in this case will be described.

Figure 13:
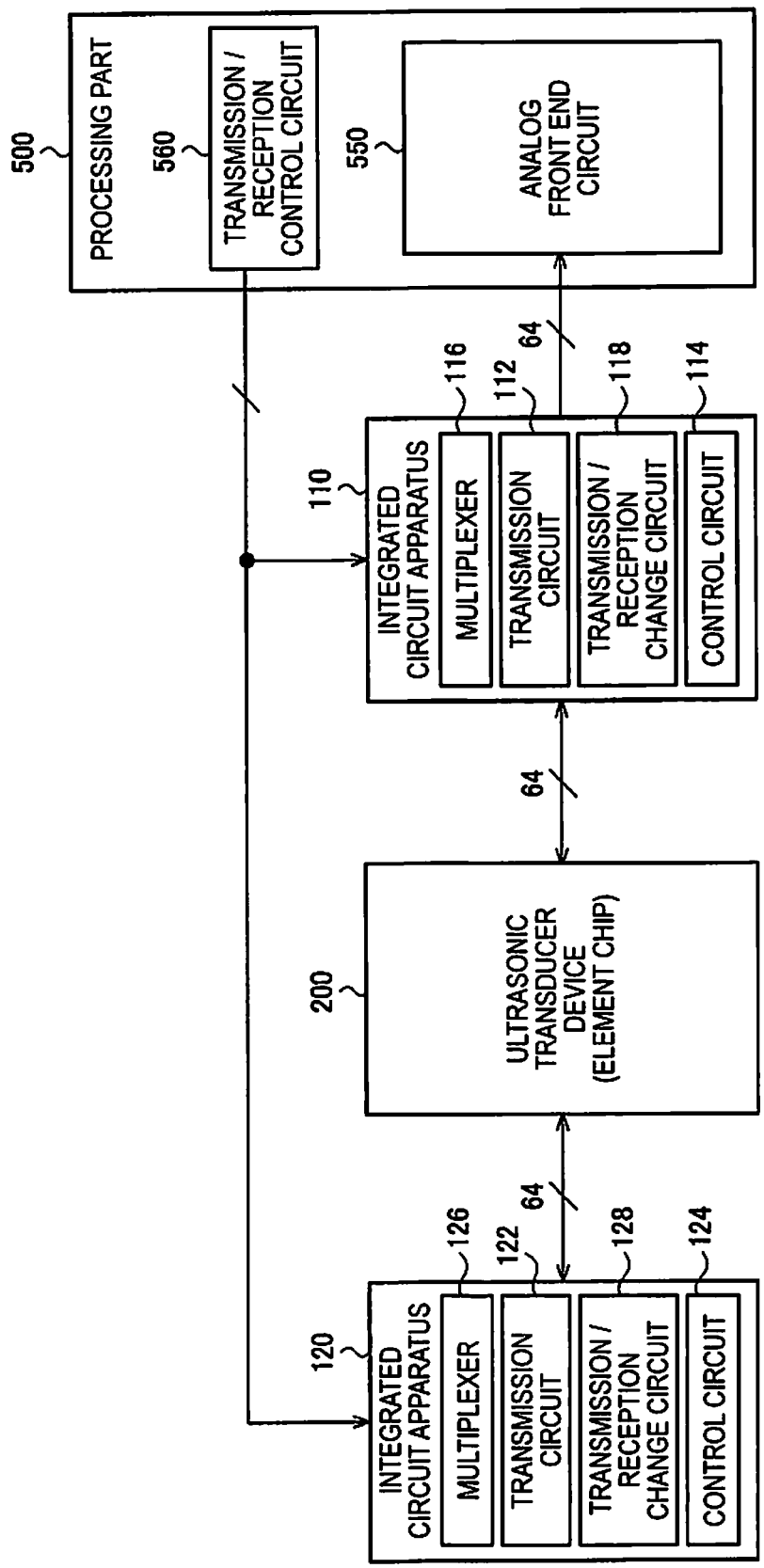
FIG. 13 shows a circuit block diagram of a second exemplary configuration of an ultrasonic measurement apparatus.

FIG. 13 shows a circuit block diagram of an exemplary configuration of an ultrasonic measurement apparatus. This ultrasonic measurement apparatus includes the element chip 200, the integrated circuit apparatuses 110 and 120, and the processing part 500. The processing part 500 includes the analog front end circuit 550 and the transmission/reception control circuit 560. Note that the same reference signs are given to constituent elements that are the same as constituent elements described with FIG. 8 and the like, and description thereof will be omitted as appropriate.

The integrated circuit apparatus 110 includes a transmission circuit 112 that amplifies transmission pulse signals, a multiplexer 116 that performs transmission control of transmission signals from the transmission circuit 112 and reception control of reception signals from the element chip 200, a transmission/reception change circuit 118 that outputs reception signals from the multiplexer 116 to the analog front end circuit 550, and a control circuit 114 that controls the transmission circuit 112, the multiplexer 116 and the transmission/reception change circuit 118 based on the instructions from the transmission/reception control circuit 560. Similarly, the integrated circuit apparatus 120 includes a transmission circuit 122, a multiplexer 126, a transmission/reception change circuit 128, and a control circuit 124.

Figure 14:
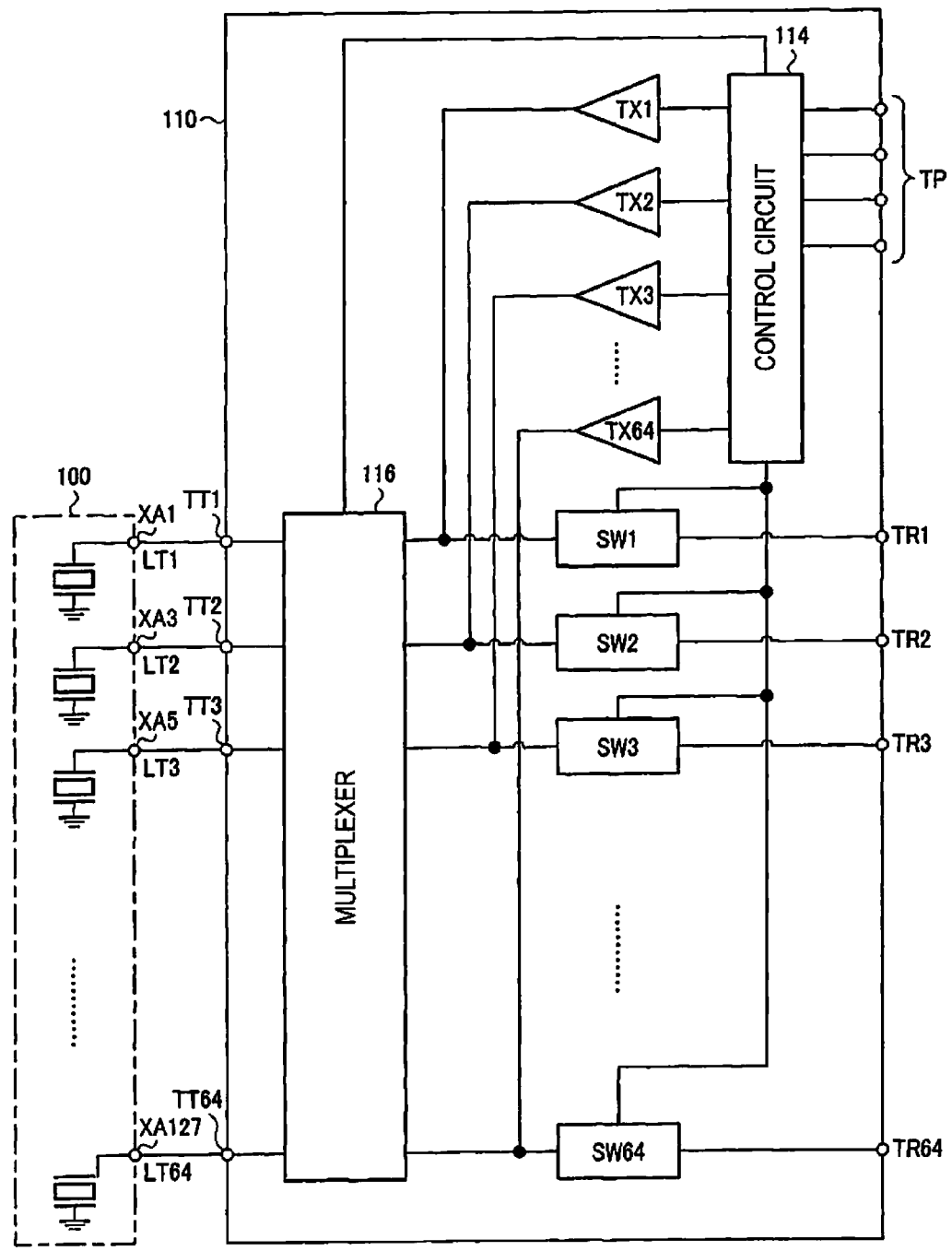
FIG. 14 shows a second detailed exemplary configuration of an integrated circuit apparatus.

FIG. 14 shows a detailed exemplary configuration of the integrated circuit apparatus 110. Note that although the integrated circuit apparatus 110 will be given as an example, the integrated circuit apparatus 120 can also be constituted similarly. The integrated circuit apparatus 110 includes the transmission circuits TX1 to TX64 (pulsars), the control circuit 114, the multiplexer 116, and switch elements SW1 to SW64 (transmission/reception changeover switches). The transmission circuits TX1 to TX64 correspond to the transmission circuit 112 in FIG. 13, and the switch elements SW1 to SW64 correspond to the transmission/reception change circuit 118 in FIG. 13.

In the transmission period of ultrasonic waves, the transmission/reception control circuit 560 inputs a transmission control command to the control circuit 114 via the terminal group TP (control terminals). The control circuit 114 supplies a transmission pulse signal to the transmission circuits TX1 to TX64 based on the transmission control command. The transmission circuits TX1 to TX64 amplify the supplied transmission pulse signal, and output the amplified transmission pulse signal to the multiplexer 116. The multiplexer 116 outputs the amplified transmission pulse signal to the ultrasonic transducer element array 100 via the transmission terminals TT1 to TT64.

In the transmission period, the switch elements SW1 to SW64 are turned off based on an instruction from the control circuit 114, and the transmission pulse signals from the transmission circuits TX1 to TX64 are not output to the analog front end circuit 550. The analog front end circuit 550 generally operates with a voltage of several volts, and the transmission pulse signals are blocked so that the analog front end circuit 550 is not damaged by the transmission pulse signals which have an amplitude of around 10 to 30 V.

In the reception period of ultrasonic waves, the ultrasonic transducer element array 100 receives the reflected waves of ultrasonic waves reflected from the observation object, and reception signals are input to the multiplexer 116 via the transmission/reception terminals TT1 to TT64. The multiplexer 116 outputs the reception signals to the switch elements SW1 to SW64. The switch elements SW1 to SW64 are ON during the ultrasonic wave reception period of the ultrasonic transducer element array 100, and output reception signals to the analog front end circuit 550 via the reception signal output terminals TR1 to TR64.

12. Transmission/reception Control in Second Detailed Configuration

Transmission/reception control will be described in detail, taking the linear scanning described with FIG. 10 as an example. In the linear scanning, the transmission circuits TX5 to TR64 are set to a non-operational mode (for example, power saving mode or power down mode), and the switch elements SW5 to SW64 are turned off. The multiplexer 116 performs switching control on transmission signals and reception signals based on instructions from the control circuit 114.

Specifically, in the scanning period T1, the transmission circuits TX1 to TX4 of the integrated circuit apparatus 110 output the odd-numbered pulse signals P1, P3, P5 and P7. The multiplexer 116 outputs the pulse signals P1, P3, P5 and P7 to the channels CH1, CH3, CH5 and CH7. The transmission circuits TX1 to TX4 of the integrated circuit apparatus 120 output the even-numbered pulse signals P2, P4, P6 and P8, and the multiplexer 126 outputs the pulse signals P2, P4, P6 and P8 to the channels CH2, CH4, CH6 and CH8.

At the time of reception, the multiplexer 116 of the integrated circuit apparatus 110 outputs the reception signals of the channels CH1, CH3, CH5 and CH7 to the analog front end circuit 550 via the switch elements SW1 to SW4 of the integrated circuit apparatus 110. The multiplexer 126 of the integrated circuit apparatus 120 outputs the reception signals of the channels CH2, CH4, CH6 and CH8 to the analog front end circuit 550 via the switch elements SW1 to SW4 of the integrated circuit apparatus 120.

In the next scanning period T2, the ultrasonic beam is shifted one channel, and transmission and reception are performed using the channels CH2 to CH9. That is, the transmission circuits TX1 to TX4 of the integrated circuit apparatus 120 output the odd-numbered pulse signals P1, P3, P5 and P7, and the multiplexer 126 outputs the pulse signals P1, P3, P5 and P7 to the channels CH2, CH4, CH6 and CH8. Also, the transmission circuits TX1 to TX4 of the integrated circuit apparatus 110 output the even-numbered pulse signals P2, P4, P6 and P8, and the multiplexer 116 outputs the pulse signals P2, P4, P6 and P8 to the channels CH3, CH5, CH7 and CH9.

At the time of reception, the multiplexer 126 of the integrated circuit apparatus 120 outputs the reception signals of the channels CH2, CH4, CH6 and CH8 to the analog front end circuit 550 via the switch elements SW1 to SW4 of the integrated circuit apparatus 120. The multiplexer 116 of the integrated circuit apparatus 110 outputs the reception signals of the channels CH3, CH5, CH7 and CH9 to the analog front end circuit 550 via the switch elements SW1 to SW4 of the integrated circuit apparatus 110.

In the subsequent scanning periods T3, T4, . . . , multiplexer 116 shifts the ultrasonic beam one channel at a time, and performs similar transmission/reception control.

Note that, in the present embodiment, the scanning operation is not limited to linear scanning, and sector scanning (phase scanning) may be performed, for example. In the case of performing sector scanning, the transmission circuits TX1 to TX64 output pulse signals at the time of transmission, and the switch elements SW1 to SW64 are turned ON at the time of reception.

Also, although a configuration having transmission circuits and switch elements for 64 channels (half of the 128 channels of the element chip 200) has been described as an example with FIG. 14, the present embodiment is not limited thereto. For example, in the case of performing linear scanning, a configuration having transmission circuits and switch elements for 4 channels (half of the 8 channels that output one ultrasonic beam) may be adopted.

In this way, with the ultrasonic measurement apparatus of the present embodiment, the number of transmission circuits and switch elements (and the number of terminals corresponding thereto) can be constituted in various combinations, according to the scanning mode, the number of drive channels, the number of reception channels, and the like.

Also, in the present embodiment, a configuration in which the multiplexers 116 and 126 are omitted may be adopted. In this case, when performing linear scanning, the transmission circuit that outputs a transmission signal is changed over sequentially every scanning period, similarly to the transmission operation described with FIG. 9. At the time of reception, the switch elements SW1 to SW4 of the integrated circuit apparatus 110 and the switch elements SW1 to SW4 of the integrated circuit apparatus 120 allow the reception signals of the channels CH1 to CH8 to pass in the scanning period T1. In the next scanning period T2, the switch elements SW1 to SW4 of the integrated circuit apparatus 120 and the switch elements SW2 to SW5 of the integrated circuit apparatus 110 allow the reception signals of the channels CH2 to CH9 to pass. In this way, the switch element that is ON is changed over sequentially.

13. Second Layout Configuration of Integrated Circuit Apparatus

Figure 15:
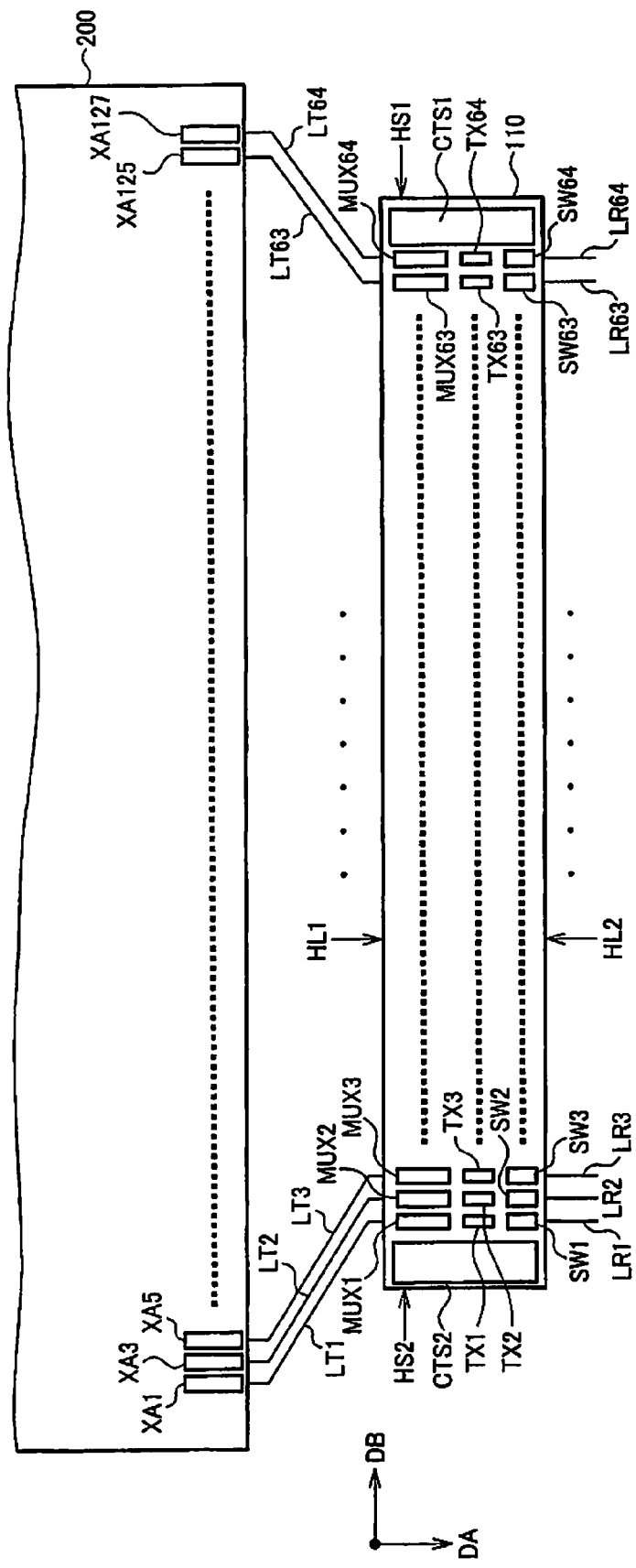
FIG. 15 shows a second exemplary layout configuration of an integrated circuit apparatus.

FIG. 15 shows a second exemplary layout configuration of the integrated circuit apparatus 110. Although the integrated circuit apparatus 110 will be given hereinafter as an example, the integrated circuit apparatus 120 can also be constituted similarly. The integrated circuit apparatus 110 includes multiplexers MUX1 to MUX64, transmission circuits TX1 to TX64, switch elements SW1 to SW64, and control circuits CTS1 and CTS2. Note that the multiplexers MUX1 to MUX64 correspond to the multiplexer 116 in FIG. 14, and the control circuits CTS1 and CTS2 correspond to the control circuit 114 in FIG. 14.

The multiplexers MUX1 to MUX64 are arrayed along the first long side HL1 of the integrated circuit apparatus 110. The multiplexers MUX may be arranged in cells as shown in FIG. 15, or may be formed as one circuit block. The multiplexers MUX, in the case of being formed as one circuit block, are arranged such that the long side of the circuit block lies along the first long side HL1. By arranging the multiplexers in this way, the multiplexers MUX1 to MUX64 can be arranged in close proximity corresponding to the transmission/reception terminals TT1 to TT64, enabling an efficient layout to be realized.

The switch elements SW1 to SW64 are arrayed along the second long side HL2 of the integrated circuit apparatus 110. The reception signal output terminals TR1 to TR64 are arrayed along the second long side HL2. The switch elements SW1 to SW64 are arranged in cells as shown in FIG. 15. Since the switch elements SW1 to SW64 can be arranged in close proximity corresponding to the reception signal output terminals TR1 to TR64, an efficient layout can be realized.

One end of the reception signal lines LR1 to LR64 is connected to the reception signal output terminals TR1 to TR64. The reception signals from the switch elements SW1 to SW64 are output to the analog front end circuit 550 from the other end of the reception signal lines LR1 to LR64. The reception signal lines LR1 to LR64 are wired in the direction DA.

The transmission circuits TX1 to TX64 are arranged in the long-side direction, between the multiplexers MUX1 to MUX64 and the switch elements SW1 to SW64. The transmission circuits TX1 to TX64 are arranged in cells as shown in FIG. 15.

The control circuit CTS1 is arranged on the first short side HS1 side of the integrated circuit apparatus 110, and the control circuit CTS2 is arranged on the second short side HS2 side of the integrated circuit apparatus 110. By arranging the control circuits CTS1 and CTS2 on the short sides in this way, the control terminals can be arranged on the short side, and the short sides can be utilized effectively while maintaining the long narrow form in the long-side direction.

Note that although, in the above embodiment, the cases where the integrated circuit apparatuses 110 and 120 perform only transmission and perform both transmission and reception were described as examples, the present embodiment is not limited thereto, and the integrated circuit apparatuses 110 and 120 need only perform at least one of transmission and reception. For example, the integrated circuit apparatus 110 may perform only transmission and the integrated circuit apparatus 120 may perform only reception. In this case, transmission is performed with the 64 odd-numbered channels, and reception is performed with the 64 even-numbered channels. Analog front end circuits such as reception signal amplification circuits, A/D conversion circuits or the like, for example, are envisaged as the reception circuits that are integrated in the integrated circuit apparatus 120.

14. Exemplary Modified Configurations of the Channels

Although, in FIGS. 5A and 5B, the case where ultrasonic transducer elements are connected in parallel between the channel terminals XAi and the common terminals XCi was described as an example, the present embodiment is not limited thereto.

Figure 16:
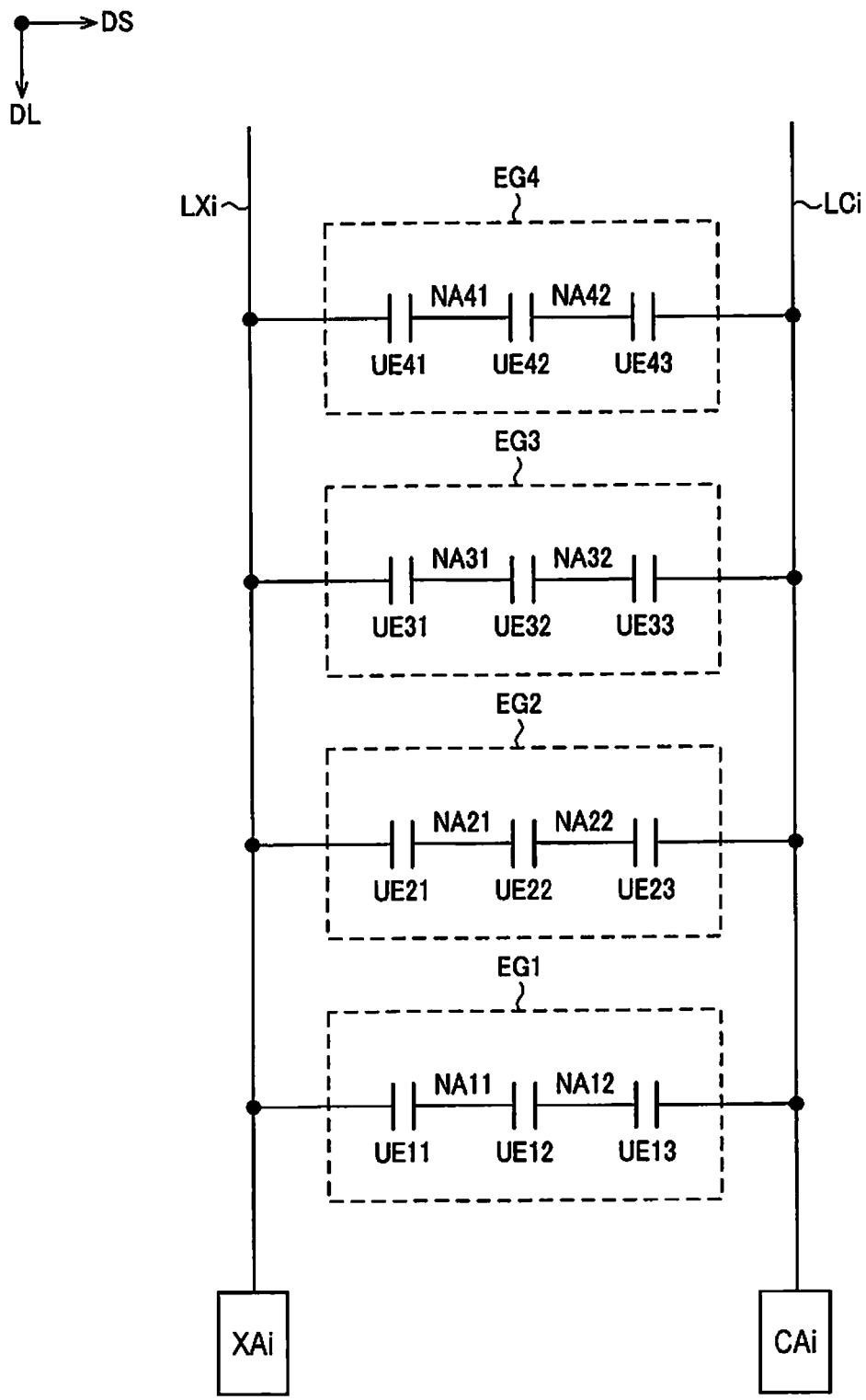
FIG. 16 shows a first exemplary modified configuration of a channel.

A first exemplary modified configuration of the channels CHi (channel element group) is shown in FIG. 16. Each channel CHi includes element groups EG1 to EGm (where m is a natural number such that m≥2) that are connected in parallel between the signal electrode line LXi and the common electrode line LCi. Note that although the case where m=4 will be described hereinafter as an example, the present embodiment is not limited thereto.

Each element group of the element groups EG1 to EG4 has j ultrasonic transducer elements 10 (where j is a natural number such that j≥2) connected in series. Note that although the case where j=3 will be described hereinafter as an example, the present embodiment is not limited thereto. Specifically, an element group EGt (where t is a natural number such that t≤4=m) has an ultrasonic transducer element UEt1 that is provided between the signal electrode line LXi and a node NAt1, an ultrasonic transducer element UEt2 that is provided between the node NAt1 and a node NAt2, and an ultrasonic transducer element UEt3 that is provided between the node NAt2 and the common electrode line LCi.

The ultrasonic transducer elements UEt1 to UEt3 of each element group EGt are arranged in the scan direction DS, and the element groups EG1 to EG4 are arranged in the slice direction DL. Specifically, the sth ultrasonic transducer elements UE1s, UE2s, UE3s and UE4s (where s is a natural number such that s≤3=j) of the element groups EG1 to EG4 are arranged in the slice direction DL.

According to the above first modification, each channel CHi (or CHi+1) has the 1st to mth element groups EG1 to EG4 (where m=4; m can be a natural number of 2 or more). The plurality of ultrasonic transducer elements that are included in each of the 1st to mth element groups EG1 to EG4 are electrically connected in series within the element group. The 1st to mth element groups EG1 to EG4 are electrically connected in parallel.

According to this configuration, because a plurality of ultrasonic transducer elements are connected in series between the terminals XAi and XCi in each element group, the amplitudes of the reception voltages of the plurality of ultrasonic transducer elements are added together, enabling reception sensitivity to be improved. Also, transmission sound pressure can be increased by connecting the element groups EG1 to EG4 in parallel. An increase in transmission sound pressure can thereby be achieved together with an improvement in reception sensitivity, enabling minute echoes from deep in the human body to be received with a high S/N, while suppressing the influence of transmitted ultrasonic waves on the human body.

Figure 17:
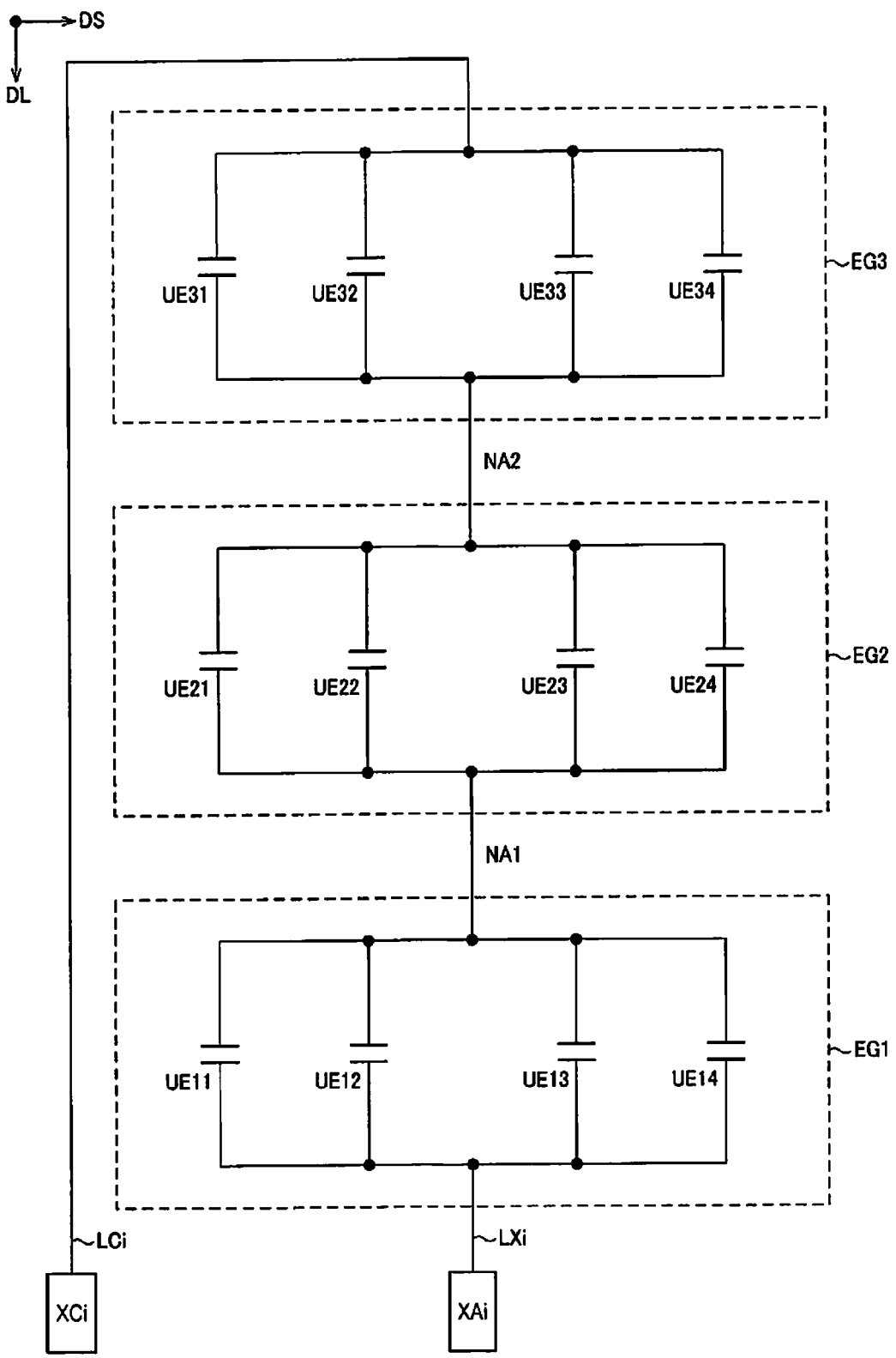
FIG. 17 shows a second exemplary modified configuration of a channel.

A second exemplary modified configuration of the channels CHi is shown in FIG. 17. Each channel CHi includes the element groups EG1 to EGm (where m is a natural number such that m≥2) which are connected in series between the signal electrode line LXi and the common electrode line LCi. Note that although the case where m=3 will be described hereinafter as an example, the present embodiment is not limited thereto.

Each element group of the element groups EG1 to EG3 has j ultrasonic transducer elements 10 (where j is a natural number such that j≥2) connected in parallel. Note that although the case where j=4 will be described hereinafter as an example, the present embodiment is not limited thereto. Specifically, the element group EG1 has ultrasonic transducer elements UE11 to UE14 that are connected in parallel between the signal electrode line LXi and a node NA1, the element group EG2 has ultrasonic transducer elements UE21 to UE24 that are connected in parallel between the node NA1 and a node NA2, and the element group EG3 has ultrasonic transducer elements UE31 to UE34 that are connected in parallel between the node NA2 and the common electrode line LCi.

The ultrasonic transducer elements UE11 to UE14, UE21 to UE24, and UE31 to UE34 of the respective element groups are arranged in the scan direction DS, and the element groups EG1 to EG3 are arranged in the slice direction DL. Specifically, ultrasonic transducer elements UE1s, UE2s and UE3s (where s is a natural number such that s≤4=j) are arranged in the slice direction DL.

According to the above second modification, each channel CHi (or CHi+1) has 1st to mth element groups EG1 to EG3 (where m=3; m can be a natural number of 2 or more). The plurality of ultrasonic transducer elements included in each of the 1st to mth element groups EG1 to EG3 are electrically connected in parallel within the element group. The 1st to mth element groups EG1 to EG3 are electrically connected in series.

According to this configuration, because the element groups EG1 to EG3 are connected in series between the terminals XAi and XCi, the amplitudes of the reception voltages of the element groups EG1 to EG3 are added together, enabling reception sensitivity to be improved. Also, transmission sound pressure can be increased by connecting the ultrasonic transducer elements of each element group in parallel. An increase in transmission sound pressure can thereby be achieved together with an improvement in reception sensitivity, enabling minute echoes from deep in the human body to be received with a high S/N, while suppressing the influence of transmitted ultrasonic waves on the human body.

15. Head Unit

Figure 18:
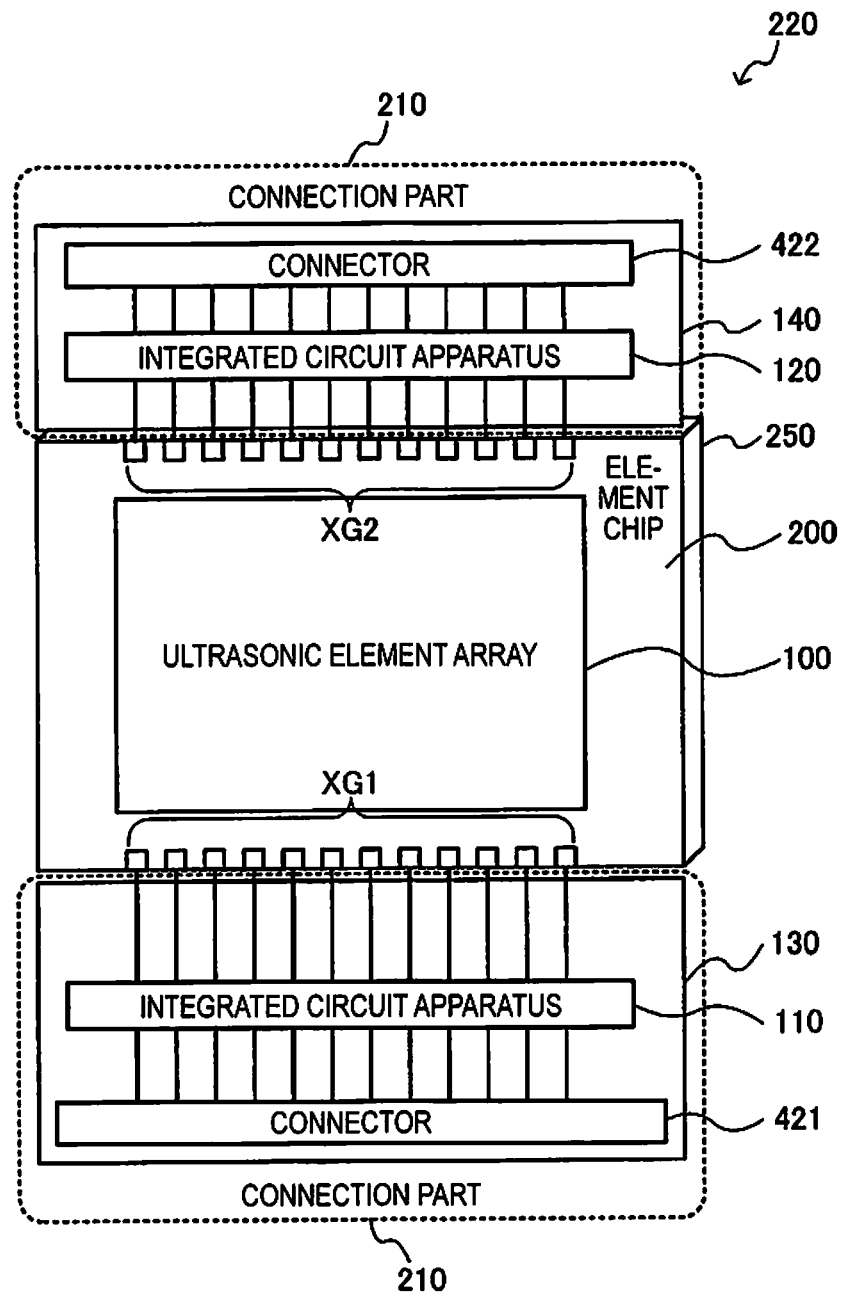
FIG. 18 shows an exemplary configuration of a head unit.

FIG. 18 shows an exemplary configuration of a head unit 220 in which the ultrasonic measurement apparatus of the present embodiment is installed. The head unit 220 shown in FIG. 18 includes the element chip 200, a connection part 210, and a supporting member 250.

The element chip 200 corresponds to the ultrasonic transducer device described with FIG. 4. The element chip 200 includes the ultrasonic transducer element array 100, a first chip terminal group XG1 (odd-numbered channel terminals XAi, common terminals XCi), and a second chip terminal group XG2 (even-numbered channel terminals XAi+1, common terminals XCi+1). The element chip 200 is electrically connected to a processing apparatus (for example, processing apparatus 330 in FIG. 21) that is included in the probe body via the connection part 210.

The connection part 210 electrically connects the probe body and the head unit 220, and has connectors 421 and 422 having a plurality of connection terminals, and flexible substrates 130 and 140 on which the connectors 421 and 422 are provided. A first wiring group that connects the first chip terminal group XG1 and the terminal group of the connector 421 that are provided on a first side of the element chip 200 is formed on the flexible substrate 130. Also, the integrated circuit apparatus 110 is flip chip mounted on the flexible substrate 130. A second wiring group that connects the second chip terminal group XG2 and the terminal group of the connector 422 that are provided on a second side of the element chip 200 is formed on the flexible substrate 140. Also, the integrated circuit apparatus 120 is flip chip mounted on the flexible substrate 140.

Note that the connection part 210 is not limited to the configuration shown in FIG. 18. For example, a first connection terminal group may be provided on the flexible substrate 130, instead of the connector 421. Also, a second connection terminal group may be provided on the flexible substrate 140, instead of the connector 422.

By providing the connection part 210, the probe body and the head unit 220 can be electrically connected, and the head unit 220 can be configured to be detachable from the probe body.

The supporting member 250 is a member that supports the element chip 200, and, as will be discussed later, a plurality of connection terminals are provided on a first surface side of the supporting member 250, and the element chip 200 is supported at a second surface side that is the opposite surface to the first surface of the supporting member 250. Note that specific structures of the element chip 200, the connection part 210, and the supporting member 250 will be discussed later.

A detailed exemplary configuration of the head unit 220 is shown in FIGS. 19A to 19C. FIG. 19A shows a second surface SF2 side of the supporting member 250, FIG. 19B shows a first surface SF1 side of the supporting member 250, and FIG. 19C shows the lateral surface side of the supporting member 250.

The connectors 421 and 422 are provided on the first surface SF1 side of the supporting member 250. Connectors 421 and 422 can be detachably attached to corresponding connectors on the probe body.

The element chip 200 is supported on the second surface SF2 side, which is the opposite surface to the first surface SF1 of the supporting member 250. The other end of the flexible substrates 130 and 140 is connected to the terminals of the element chip 200. Fixing members 260 are provided on each corner portion of the supporting member 250, and are used for fixing the head unit 220 to the probe casing.

As shown in FIG. 19C, a protective member 270 (protective film) that protects the element chip 200 is provided on the surface of the element chip 200 (surface on which the piezoelectric layer 30 is formed in FIG. 3B).

16. Ultrasonic Probe

Figure 20A:
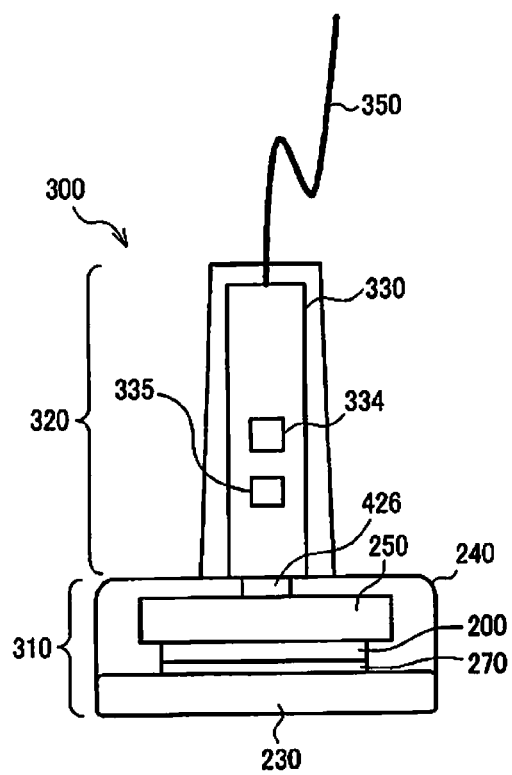
FIGS. 20A and 20B show an exemplary configuration of an ultrasonic probe.
Figure 20B:
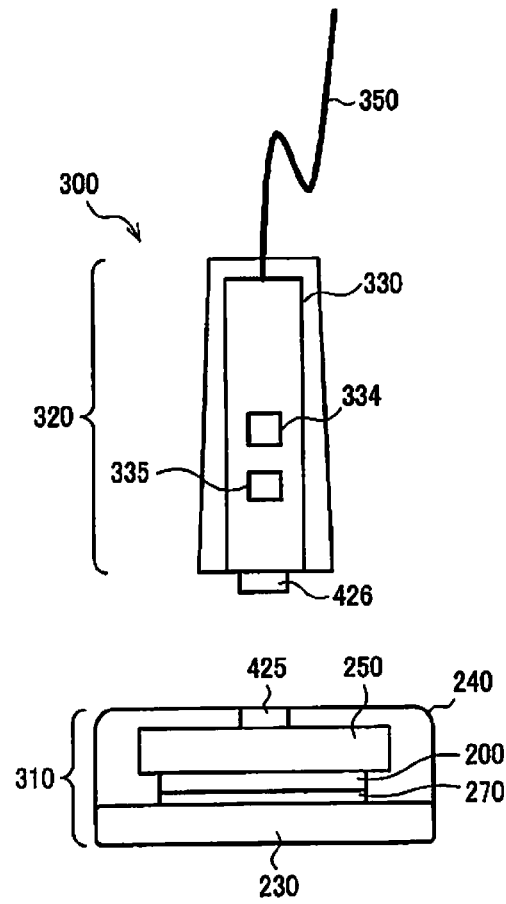

An exemplary configuration of an ultrasonic probe 300 to which the above head unit 220 is applied is shown in FIGS. 20A and 20B. FIG. 20A shows the case where a probe body 320 is mounted on a probe head 310, and FIG. 20B shows the case where the probe head 310 is removed from the probe body 320.

The probe head 310 includes a head unit 220 and a probe casing 240 storing the head unit 220 and a contact member 230 that contacts the sample. The element chip 200 is provided between the contact member 230 and the supporting member 250.

The probe body 320 includes a processing apparatus 330 and a connector 426 on the probe body side. The processing apparatus 330 includes a reception part 335 (analog front end part) and a transmission/reception control part 334. The reception part 335 performs reception processing of ultrasonic echo signals (reception signals) from the ultrasonic transducer elements. The transmission/reception control part 334 performs control of the integrated circuit apparatuses 110 and 120 and the reception part 335. The connector 426 on the probe body side is connected to a connector 425 on the head unit side. The probe body 320 is connected to the main body of an electronic device (for example, ultrasonic imaging apparatus) by a cable 350.

Although the head unit 220 is stored in the probe casing 240, the head unit 220 can be removed from the probe casing 240. This enables only the head unit 220 to be replaced. Alternatively, the head unit 220 can also be replaced in a state of being stored in the probe casing 240, that is, along with the probe head 310.

17. Ultrasonic Imaging Apparatus

Figure 21:
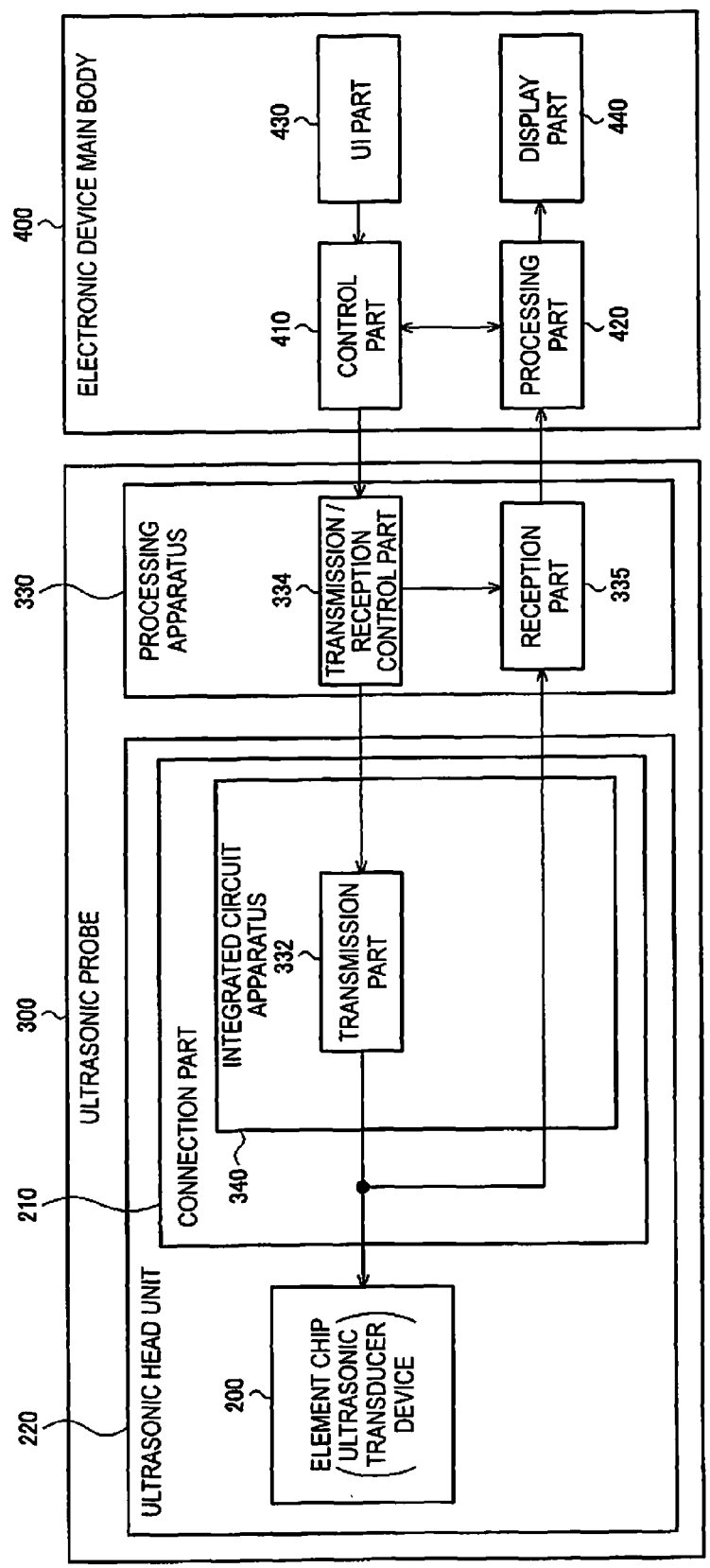
FIG. 21 shows an exemplary configuration of an ultrasonic imaging apparatus.

FIG. 21 shows an exemplary configuration of an ultrasonic imaging apparatus. The ultrasonic imaging apparatus includes the ultrasonic probe 300 and an electronic device main body 400. The ultrasonic probe 300 includes the ultrasonic head unit 220 and the processing apparatus 330. The electronic device main body 400 includes a control part 410, a processing part 420, a user interface part 430, and a display part 440.

The processing apparatus 330 includes the transmission/reception control part 334 and the reception part 335 (analog front end part). The ultrasonic head unit 220 includes the element chip 200 (ultrasonic transducer element), and the connection part 210 (connector part) which connects the element chip 200 to a circuit board (for example, rigid board). The transmission/reception control part 334 and the reception part 335 are mounted on the circuit board. The connection part 210 includes an integrated circuit apparatus 340. The integrated circuit apparatus 340 includes a transmission part 332. Note that the integrated circuit apparatus 340 corresponds to the integrated circuit apparatuses 110 and 120.

In the case of transmitting ultrasonic waves, the transmission/reception control part 334 issues a transmission instruction to the transmission part 332, and the transmission part 332 amplifies a drive signal to the high voltage after receiving the transmission instruction, and outputs a drive voltage. The reception part 335 has a limiter circuit which is not illustrated, and the limiter circuit blocks the drive voltage. In the case of receiving a reflected wave of ultrasonic waves, the reception part 335 receives the signal of the reflected wave detected by the element chip 200. The reception part 335 performs processing on the signal of the reflected waves (for example, amplification, A/D conversion, etc.), based on a reception instruction from the transmission/reception control part 334, and transmits the processed signal to the processing part 420. The processing part 420 converts the signal into a video signal, and displays the video signal on the display part 440.

Note that the ultrasonic measurement apparatus of the present embodiment is applicable not only to an ultrasonic imaging apparatus for medical use such as described above but to various electronic devices. For example, devices such as diagnostic devices that perform non-destructive examination of the inside of buildings or the like, and user interface devices that detect the motion of a user's finger via reflection of ultrasonic waves are envisaged as electronic devices to which the ultrasonic transducer device can be applied.

Note that although the present embodiment has been described in detail above, a person skilled in the art will appreciate that numerous modifications can be made without substantially departing from the novel matter and effects of the invention. Accordingly, all such modifications are within the scope of the invention. For example, terms that appear in the description or drawings at least once together with other broader or synonymous terms can be replaced by those other terms at any place within the description or drawings. All combinations of the present embodiment and the modifications are also within the scope of the invention. Also, the configurations and operations of the integrated circuit apparatus, the ultrasonic transducer element, the ultrasonic transducer device, the ultrasonic head unit, the ultrasonic probe and the ultrasonic imaging apparatus, the method of mounting the integrated circuit apparatus, the method of scanning an ultrasonic beam, and the like are not limited to those described in this embodiment, and various modifications can be made.

The entire disclosure of Japanese Patent Application No. 2013-155347, filed Jul. 26, 2013 is expressly incorporated by reference herein.

What is claimed is:

1. An ultrasonic measuring apparatus comprising:
   an ultrasonic transducer device having a substrate and an ultrasonic transducer element array that is arranged on the substrate;
   a first channel terminal group arranged at one edge portion of the ultrasonic transducer element array in a first direction;
   a second channel terminal group arranged at the other edge portion of the ultrasonic transducer element array in the first direction;
   a first flexible substrate provided on the one edge portion side, and having arranged thereon a first wiring group that is connected to the first channel terminal group;
   a first integrated circuit apparatus that is mounted on the first flexible substrate, and performs at least one of signal transmission to the first channel terminal group and signal reception from the first channel terminal group;
   a second flexible substrate provided on the other edge portion side, and having arranged thereon a second wiring group that is connected to the second channel terminal group; and
   a second integrated circuit apparatus that is mounted on the second flexible substrate, and performs at least one of signal transmission to the second channel terminal group and signal reception from the second channel terminal group,
   wherein, in the ultrasonic transducer element array, channels that are connected to the first channel terminal group and channels that are connected to the second channel terminal group are arranged alternately every channel in a second direction that intersects the first direction.

2. The ultrasonic measurement apparatus according to claim 1,
   wherein, in a first scanning period, the first integrated circuit apparatus transmits odd-numbered pulse signals, among 1st to kth pulse signals (where k is a natural number of 2 or more) to channel terminals belonging to the first channel terminal group, among 1st to kth channel terminals, and the second integrated circuit apparatus transmits even-numbered pulse signals, among the 1st to kth pulse signals, to channel terminals belonging to the second channel terminal group, among the 1st to kth channel terminals, and
   in a second scanning period subsequent to the first scanning period, the second integrated circuit apparatus transmits the odd-numbered pulse signals to channel terminals belonging to the second channel terminal group, among 2nd to k+1th channels, and the first integrated circuit apparatus transmits the even-numbered pulse signals to channels belonging to the first channel terminal group, among the 2nd to k+1th channels.

3. The ultrasonic measurement apparatus according to claim 2, comprising:
   a processing part that outputs a control command for controlling transmission in the first scanning period and the second scanning period to the first integrated circuit apparatus and the second integrated circuit apparatus,
   wherein the first integrated circuit apparatus and the second integrated circuit apparatus each include:
   a plurality of transmission circuits that transmit pulse signals; and
   a control part that controls the plurality of transmission circuits based on the control command.

4. The ultrasonic measurement apparatus according to claim 1, comprising:
a processing part that performs reception processing of reception signals,
wherein the processing part performs the reception processing, based on the reception signals from the first channel terminal group and the reception signals from the second channel terminal group obtained by the first integrated circuit apparatus and the second integrated circuit apparatus transmitting signals.

5. The ultrasonic measurement apparatus according to claim 1,
wherein, in the ultrasonic transducer element array, 1st to Nth channels (where N is a natural number of 2 or more) are arranged in the second direction,
the first channel terminal group is connected to odd-numbered channels, among the 1st to Nth channels, and
the second channel terminal group is connected to even-numbered channels, among the 1st to Nth channels.

6. The ultrasonic measurement apparatus according to claim 1,
wherein the first integrated circuit apparatus is mounted such that a long-side direction of the first integrated circuit apparatus coincides with a third direction that is a direction coinciding with the edge connecting the first flexible substrate to the first channel terminal group, and
the second integrated circuit apparatus is mounted such that a long-side direction of the second integrated circuit apparatus coincides with a fourth direction that is a direction coinciding with the edge connecting the second flexible substrate to the second channel terminal group.

7. The ultrasonic measurement apparatus according to claim 6,
wherein the first integrated circuit apparatus has a plurality of transmission circuits that are arranged in the third direction and transmit a signal to the first channel terminal group, and
the second integrated circuit apparatus has a plurality of transmission circuits that are arranged in the fourth direction and transmit a signal to the second channel terminal group.

8. The ultrasonic measurement apparatus according to claim 1,
wherein the first integrated circuit apparatus is flip chip mounted on the first flexible substrate, and
the second integrated circuit apparatus is flip chip mounted on the second flexible substrate.

9. The ultrasonic measurement apparatus according to claim 1,
wherein the channels include a 1st element group to an mth element group (where m is a natural number of 2 or more),
the plurality of ultrasonic transducer elements included in each of the 1st element group to the mth element group are electrically connected in parallel within the element group, and
the 1st element group to the mth element group are electrically connected in series.

10. The ultrasonic measurement apparatus according to claim 1,
wherein the channels include a 1st element group to an mth element group (where m is a natural number of 2 or more),
the plurality of ultrasonic transducer elements included in each of the 1st element group to the mth element group are electrically connected in series within the element group, and
the 1st element group to the mth element group are electrically connected in parallel.

11. The ultrasonic measurement apparatus according to claim 1,
wherein the first flexible substrate has a plurality of openings arranged in an array,
the ultrasonic transducer element array has an ultrasonic transducer element for each of the plurality of openings,
the ultrasonic transducer elements each include:
a vibration film that closes a corresponding opening among the plurality of openings; and
a piezoelectric element part that is provided on the vibration film, and
the piezoelectric element part includes:
a lower electrode that is provided on the vibration film;
a piezoelectric layer that is provided so as to cover at least a portion of the lower electrode; and
an upper electrode that is provided so as to cover at least a portion of the piezoelectric layer.

12. An ultrasonic head unit comprising the ultrasonic measurement apparatus according to claim 1.

13. An ultrasonic probe comprising the ultrasonic measurement apparatus according to claim 1.

14. An ultrasonic imaging apparatus comprising:
the ultrasonic probe according to claim 13; and
a display part that displays image data for display.

* * * * *